US009610436B2

(12) United States Patent
Seifert et al.

(10) Patent No.: US 9,610,436 B2
(45) Date of Patent: Apr. 4, 2017

(54) IMPLANT TOOLS WITH ATTACHMENT FEATURE AND MULTI-POSITIONAL SHEATH AND IMPLANT TECHNIQUES UTILIZING SUCH TOOLS

(71) Applicant: Medtronic, Inc., Minneapolis, MN (US)

(72) Inventors: Kevin R. Seifert, Forest Lake, MN (US); Roger A. Christopherson, Vadnais Heights, MN (US); Nathan L. Olson, Shoreview, MN (US); Rebecca L. Poindexter, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 116 days.

(21) Appl. No.: 14/196,443

(22) Filed: Mar. 4, 2014

(65) Prior Publication Data

US 2015/0133954 A1 May 14, 2015

Related U.S. Application Data

(60) Provisional application No. 61/903,139, filed on Nov. 12, 2013.

(51) Int. Cl.
*A61B 19/00* (2006.01)
*A61N 1/05* (2006.01)
(Continued)

(52) U.S. Cl.
CPC ........ *A61N 1/0504* (2013.01); *A61B 17/3415* (2013.01); *A61B 17/3468* (2013.01);
(Continued)

(58) Field of Classification Search
CPC ........ A61F 2/01; A61F 2002/011; A61F 2/95; A61B 17/3468; A61B 2017/00349;
(Continued)

(56) References Cited

U.S. PATENT DOCUMENTS 4,030,509 A   6/1977  Heilman et al.
4,146,037 A   3/1979  Flynn et al.
(Continued)

FOREIGN PATENT DOCUMENTS

| EP | 0517494 A2 | 12/1992 |
|---|---|---|
| WO | 9720530 A1 | 6/1997 |
| WO | 0123035 A1 | 4/2001 |
| WO | 2004073506 A2 | 9/2004 |
| WO | 2010045228 A2 | 4/2010 |
| WO | WO 2013/076213 | * 5/2013 |

OTHER PUBLICATIONS

Tung et al., "Minimal Invasive Extra Cardiac Placement of High Voltage Defibrillator Leads", Poster 3; S200 Abstract, PO-3-4; St. Paul Hospital, Vancouver, British Columbia, Canada, 1 page.
(Continued)

*Primary Examiner* — Katherine M Shi

(57) ABSTRACT

Implant tools and techniques for implantation of a medical lead, catheter or other implantable component are provided. The implant tools and techniques are particularly useful in implanting medical electrical leads in extravascular locations, including subcutaneous locations. An example implant tool for implanting a medical lead includes a rod and a sheath configured to be placed on the rod. The rod includes a handle, a shaft having a proximal end adjacent to the handle and a distal end, and an attachment feature toward the distal end of the shaft, the attachment feature configured to couple to the medical lead. The sheath is configured to be placed in multiple positions along the rod including a first position in which the sheath does not interact with the attachment feature and second position in which the sheath does interact with the attachment feature.

22 Claims, 32 Drawing Sheets

(51) Int. Cl.
*A61B 17/34* (2006.01)
*A61M 25/06* (2006.01)
*A61B 17/00* (2006.01)
*A61B 17/32* (2006.01)
*A61B 90/00* (2016.01)

(52) U.S. Cl.
CPC .............. *A61B 2017/00243* (2013.01); *A61B 2017/00349* (2013.01); *A61B 2017/320056* (2013.01); *A61B 2090/0811* (2016.02); *A61M 25/0662* (2013.01); *A61N 1/0563* (2013.01)

(58) Field of Classification Search
CPC ...... A61B 2017/06052; A61B 17/0469; A61B 17/0483; A61B 17/0485; A61N 1/05; A61N 1/0504; A61M 25/0668
USPC .............. 606/108, 129, 144, 148, 200, 145; 607/116, 119
See application file for complete search history.

(56) References Cited

U.S. PATENT DOCUMENTS

| | | |
|---|---|---|
| 4,270,549 A | 6/1981 | Heilman |
| 4,280,510 A | 7/1981 | O'Neill |
| 4,291,707 A | 9/1981 | Heilman et al. |
| 4,424,818 A | 1/1984 | Doring et al. |
| 4,437,475 A | 3/1984 | White |
| 4,512,351 A | 4/1985 | Pohndorf |
| 4,538,624 A | 9/1985 | Tarjan |
| 4,644,957 A | 2/1987 | Ricciardelli et al. |
| 4,765,341 A | 8/1988 | Mower et al. |
| 4,832,687 A | 5/1989 | Smith, III |
| 5,036,854 A | 8/1991 | Schollmeyer et al. |
| 5,125,904 A | 6/1992 | Lee |
| 5,176,135 A | 1/1993 | Fain et al. |
| 5,255,691 A | 10/1993 | Otten |
| 5,300,106 A | 4/1994 | Dahl et al. |
| 5,312,355 A | 5/1994 | Lee |
| 5,346,502 A * | 9/1994 | Estabrook ...... A61B 17/320068 601/2 |
| 5,441,504 A | 8/1995 | Pohndorf et al. |
| 5,456,699 A | 10/1995 | Armstrong |
| 5,509,924 A | 4/1996 | Paspa et al. |
| 5,613,953 A | 3/1997 | Pohndorf |
| 5,667,514 A | 9/1997 | Heller |
| 5,671,736 A | 9/1997 | Pettit et al. |
| 5,690,648 A | 11/1997 | Fogarty et al. |
| 5,752,937 A | 5/1998 | Otten et al. |
| 5,779,715 A * | 7/1998 | Tu .......................... A61B 17/50 606/108 |
| 5,782,841 A | 7/1998 | Ritz |
| 5,871,528 A | 2/1999 | Camps et al. |
| 5,944,732 A | 8/1999 | Raulerson et al. |
| 5,951,518 A | 9/1999 | Licata et al. |
| 6,032,079 A | 2/2000 | KenKnight et al. |
| 6,104,957 A | 8/2000 | Alo et al. |
| 6,122,552 A | 9/2000 | Tockman et al. |
| 6,159,198 A | 12/2000 | Gardeski et al. |
| 6,228,052 B1 | 5/2001 | Pohndorf |
| 6,324,414 B1 | 11/2001 | Gibbons et al. |
| 6,415,187 B1 | 7/2002 | Kuzma et al. |
| 6,436,068 B1 | 8/2002 | Bardy |
| 6,445,954 B1 | 9/2002 | Olive et al. |
| 6,544,247 B1 | 4/2003 | Gardeski et al. |
| 6,605,094 B1 | 8/2003 | Mann et al. |
| 6,730,083 B2 | 5/2004 | Freigang et al. |
| 6,733,500 B2 | 5/2004 | Kelley et al. |
| 6,749,574 B2 | 6/2004 | O'Keefe |
| 6,770,070 B1 | 8/2004 | Balbierz |
| 6,772,014 B2 | 8/2004 | Coe et al. |
| 6,836,687 B2 | 12/2004 | Kelley et al. |
| 6,866,044 B2 | 3/2005 | Bardy et al. |
| 6,868,291 B1 | 3/2005 | Bonner et al. |
| 6,887,229 B1 | 5/2005 | Kurth |
| 7,001,396 B2 * | 2/2006 | Glazier ............ A61M 25/0631 604/164.03 |
| 7,033,326 B1 | 4/2006 | Pianca et al. |
| 7,069,083 B2 | 6/2006 | Finch et al. |
| 7,076,296 B2 | 7/2006 | Rissmann et al. |
| 7,117,039 B2 | 10/2006 | Manning et al. |
| 7,195,637 B2 | 3/2007 | Mika |
| 7,218,970 B2 | 5/2007 | Ley et al. |
| 7,229,450 B1 | 6/2007 | Chitre et al. |
| 7,288,096 B2 | 10/2007 | Chin |
| 7,316,667 B2 | 1/2008 | Lindstrom et al. |
| 7,322,960 B2 | 1/2008 | Yamamoto et al. |
| 7,369,899 B2 | 5/2008 | Malinowski et al. |
| 7,389,134 B1 | 6/2008 | Karicherla et al. |
| 7,450,997 B1 | 11/2008 | Pianca et al. |
| 7,499,758 B2 | 3/2009 | Cates et al. |
| 7,499,759 B2 | 3/2009 | Coe et al. |
| 7,539,542 B1 | 5/2009 | Malinowski |
| 7,627,375 B2 | 12/2009 | Bardy et al. |
| 7,655,014 B2 | 2/2010 | Ko et al. |
| 7,736,309 B2 | 6/2010 | Miller et al. |
| 7,736,330 B2 | 6/2010 | Bardy |
| 7,765,014 B2 | 7/2010 | Eversull et al. |
| 7,837,671 B2 | 11/2010 | Eversull et al. |
| 7,846,088 B2 | 12/2010 | Ness |
| 7,930,040 B1 | 4/2011 | Kelsch et al. |
| 7,983,765 B1 | 7/2011 | Doan et al. |
| 8,057,486 B2 | 11/2011 | Hansen |
| 8,060,207 B2 | 11/2011 | Wallace et al. |
| 8,065,020 B2 | 11/2011 | Ley et al. |
| 8,066,702 B2 | 11/2011 | Rittman, III et al. |
| 8,090,451 B2 | 1/2012 | Tyson, Jr. |
| 8,155,755 B2 | 4/2012 | Flynn et al. |
| 8,157,813 B2 | 4/2012 | Ko et al. |
| 8,260,436 B2 | 9/2012 | Gerber et al. |
| 8,271,094 B1 | 9/2012 | Moffitt |
| 8,280,527 B2 | 10/2012 | Eckerdal et al. |
| 8,340,779 B2 | 12/2012 | Harris et al. |
| 8,355,786 B2 | 1/2013 | Malinowski |
| 8,364,277 B2 | 1/2013 | Glukhovsky |
| 8,386,052 B2 | 2/2013 | Harris et al. |
| 8,409,233 B1 | 4/2013 | Chinn et al. |
| 8,435,208 B2 | 5/2013 | Bardy |
| 8,442,620 B2 | 5/2013 | Silipo et al. |
| 8,447,398 B2 | 5/2013 | Bardy et al. |
| 8,452,421 B2 | 5/2013 | Thenuwara et al. |
| 8,454,552 B2 | 6/2013 | Bardy |
| 8,478,424 B2 | 7/2013 | Tronnes |
| 8,478,426 B2 | 7/2013 | Barker |
| 2002/0120277 A1* | 8/2002 | Hauschild ............ A61B 17/221 606/108 |
| 2002/0120294 A1 | 8/2002 | Kroll |
| 2003/0114908 A1 | 6/2003 | Flach |
| 2003/0233115 A1 | 12/2003 | Eversull et al. |
| 2004/0054388 A1 | 3/2004 | Osypka |
| 2004/0059348 A1 | 3/2004 | Geske et al. |
| 2004/0064147 A1 | 4/2004 | Struble |
| 2004/0102829 A1 | 5/2004 | Bonner et al. |
| 2004/0176781 A1* | 9/2004 | Lindstrom ......... A61B 17/3468 606/129 |
| 2004/0210293 A1 | 10/2004 | Bardy et al. |
| 2004/0236396 A1 | 11/2004 | Coe et al. |
| 2005/0049663 A1 | 3/2005 | Harris et al. |
| 2005/0119680 A1 | 6/2005 | Dykes |
| 2005/0131505 A1 | 6/2005 | Yokoyama |
| 2005/0288758 A1 | 12/2005 | Jones et al. |
| 2006/0041295 A1 | 2/2006 | Okypka |
| 2006/0116746 A1 | 6/2006 | Chin |
| 2006/0122676 A1 | 6/2006 | Ko et al. |
| 2006/0253181 A1 | 11/2006 | Schulman et al. |
| 2006/0265047 A1* | 11/2006 | Dorn ....................... A61F 2/95 623/1.12 |
| 2007/0100409 A1 | 5/2007 | Worley et al. |
| 2007/0173900 A1 | 7/2007 | Siegel |
| 2007/0208402 A1 | 9/2007 | Helland et al. |
| 2007/0249992 A1 | 10/2007 | Bardy |
| 2008/0046056 A1 | 2/2008 | O'Connor |
| 2008/0132933 A1 | 6/2008 | Gerber |
| 2008/0132970 A1 | 6/2008 | Barolat |

(56) References Cited

U.S. PATENT DOCUMENTS

| | | | |
|---|---|---|---|
| 2008/0243219 | A1 | 10/2008 | Malinowski et al. |
| 2008/0269716 | A1 | 10/2008 | Bonde et al. |
| 2009/0076521 | A1 | 3/2009 | Hansen |
| 2009/0157091 | A1 | 6/2009 | Buysman |
| 2009/0222021 | A1 | 9/2009 | Chang |
| 2009/0259283 | A1 | 10/2009 | Brandt et al. |
| 2009/0264780 | A1 | 10/2009 | Schilling |
| 2010/0016935 | A1 | 1/2010 | Strandberg et al. |
| 2010/0030227 | A1 | 2/2010 | Kast et al. |
| 2010/0030228 | A1 | 2/2010 | Havel |
| 2010/0056858 | A1 | 3/2010 | Mokelke et al. |
| 2010/0094252 | A1 | 4/2010 | Wengreen et al. |
| 2010/0113963 | A1 | 5/2010 | Smits et al. |
| 2010/0125194 | A1 | 5/2010 | Bonner et al. |
| 2010/0137879 | A1 | 6/2010 | Ko et al. |
| 2010/0152747 | A1 | 6/2010 | Padiy et al. |
| 2010/0217298 | A1 | 8/2010 | Bardy |
| 2010/0217301 | A1 | 8/2010 | Bardy |
| 2010/0249696 | A1 | 9/2010 | Bardy |
| 2010/0305428 | A1 | 12/2010 | Bonner et al. |
| 2010/0318098 | A1 | 12/2010 | Lund et al. |
| 2011/0009877 | A1 | 1/2011 | Thenuwara et al. |
| 2011/0009933 | A1 | 1/2011 | Barker |
| 2011/0022057 | A1 | 1/2011 | Eigler et al. |
| 2011/0224680 | A1 | 9/2011 | Barker |
| 2011/0224681 | A1 | 9/2011 | McDonald |
| 2011/0257660 | A1 | 10/2011 | Jones et al. |
| 2012/0016377 | A1 | 1/2012 | Geroy |
| 2012/0029335 | A1 | 2/2012 | Sudam et al. |
| 2012/0078266 | A1 | 3/2012 | Tyson, Jr. |
| 2012/0089153 | A1 | 4/2012 | Christopherson et al. |
| 2012/0097174 | A1 | 4/2012 | Spotnitz et al. |
| 2012/0191106 | A1 | 7/2012 | Ko et al. |
| 2012/0209283 | A1 | 8/2012 | Zhu |
| 2012/0209285 | A1 | 8/2012 | Barker et al. |
| 2012/0290057 | A1 | 11/2012 | Boling et al. |
| 2013/0103049 | A1 | 4/2013 | Bonde |
| 2013/0158564 | A1 | 6/2013 | Harris et al. |
| 2013/0238067 | A1 | 9/2013 | Baudino |
| 2013/0296879 | A1 | 11/2013 | Lazeroms et al. |
| 2014/0012292 | A1* | 1/2014 | Stewart .............. A61B 17/0485 606/148 |
| 2014/0163655 | A1 | 6/2014 | Chitre |
| 2014/0276927 | A1* | 9/2014 | Barker .................... A61N 1/05 606/129 |
| 2015/0105793 | A1 | 4/2015 | Cole |
| 2015/0133951 | A1 | 5/2015 | Seifert et al. |
| 2015/0133952 | A1 | 5/2015 | Seifert et al. |
| 2015/0133953 | A1 | 5/2015 | Seifert et al. |

OTHER PUBLICATIONS

Molina et al., "An Epicardial Subxiphoid Implantable Defibrillator Lead: Superior Effectiveness After Failure of Standard Implants", From the Department of Surgery, Division of Cardiovascular and Thoracic Surgery and the Department of Medicine, Cardiac Arrhythmia Center, University of Minnesota Medical School, Minneapolis, Minnesota, Pace, vol. 27, Nov. 2004, 7 pages.

(PCT/US2014/065116) PCT Notification of Transmittal of the International Search Report and the Written Opinion of the International Searching Authority, Mailed Feb. 27, 2015; 11 pages.

(PCT/US2014/065119) PCT Notification of Transmittal of the International Search Report and the Written Opinion of the International Searching Authority, Mailed Feb. 27, 2015; 11 pages.

Obadia, et al., "New Approach for Implantation of Automatic Defibrillators Using Videothoracoscopy", Journal Ann Cardiol Angeiol (Paris); Sep. 1994; 43 (7) Abstract Only, 1 page.

Lemmer, "Defibrillator Patch Constriction, Letter to the Editor", The Annals of Thoracic Surgery, 1996, 1 page.

Ely et al., "Thoracoscopic Implantation of the Implantable Cardioverter Defibrillator", Minimally Invasive Techniques; (Can be found on the World-Wide Web at http://chestioumal.chestpubs.org on May 6, 2013); dated Jan. 1993; 2 pages.

Damiano, "Implantation of Cardioverter Defibrillators in the Post -Sternotomy Patient", The Annals of Thoracic Surgery, 1992; 53: pp. 978-983.

Piccione, et al., "Erosion of Extrapericardial Implantable Cardioverter Defibrillator Patch Through the Gastic Fundus with Fistulous Tract Information", Cardiology in Review; 2006; 14, e21-e23 pages.

Vyhmeister et al., "Simple Approach for Extrapericardial Placement of Defibrillator Patches via Median Sternotomy", The Annals of Thoracic Surgery; 1994; 57: 4 pages.

Harman et al., "Differences in the Pathological Changes in Dogs' Hearts After Defibrillation with Extrapericardial Paddles and Implanted Defibrillator Electrodes", Journal of Pacing and Clinical Electrophysiology, Feb. 1991; vol. 14; Part 2; 5 pages.

Obadia et al., "Thoracoscopic Approach to Implantable Cardioverter Defibrillator Patch Electrode Implantation", Pacing and Clinical Electrophysiology; Jun. 1996; vol. 19; 6 pages.

Shapira, et al., A Simplied Method for Implantation of Automatic Cardioverter Defibrillator in Patients with Previous Cardiac Surgery, Pacing and Clinical Electrophysiology, January Part I, 1993, vol. 16; 6 pages.

Quigley et al., "Migration of an Automatic Implantable Cardioverter-Defibrillator Patch Causing Massive Hemothorax", Journal Texas Heart Institute, Nov. 1, 1996; vol. 23, 4 pages.

Karwande et al., Bilateral Anterior Thoracotomy for Automatic Implantable Cardioverter Defibrillator Placement in Patients with Previous Sternotomy, The Annals of Thoracic Surgery; Oct. 1992; 54(4); 3 pages.

Bielefeld et al., "Thoracoscopic Placement of Implantable Cardioverter-Defibrillator Patch Leads in Sheep", Circulation; Nov. 1993, vol. 88, No. 5, Part 2; 5 pages.

Frame et al., "Long-Term Stability of Defibrillation Thresholds with Intrapericardial Defibrillator Patches", Pacing and Clinical Electrophysiology, Jan. 1993, Part II, vol. 16, 6 pages.

Lawrie et al., "Right Mini-Thoracotomy: An Adjunct to Left Subcostal Automatic Implantable Cardioverter Defibrillator Implantation", The Annals of Thoracic Surgery; 1989; 47; 4 pages.

Mitchell et al., "Experience with an Implantable Tiered Therapy Device Incorporating Antitachycardia Pacing and Cardioverter/ Defibrillator Therapy", Thoracic and Cardiovascular Surgery, Abstract Only, Mar. 1993, 1 page.

Bolling et al., "Automatic Internal Cardioverter Defibrillator: A Bridge to Heart Transplantation", Heart Lung Transplantation, Abstract Only, Jul.-Aug. 1991, 1 page.

Steinke et al., Subepicardial Infarction, Myocardial Impression, and Ventricular Penetration by Sutureless Electrode and Leads, Chest; 70: Jul. 1, 1976, 2 pages.

Avogadros Lab Supply Inc., Catalog; Scoopula with Beech Wood Handle, can be found on-line at http://www.avogadro-lab-supply.com/search.php, accessed Oct. 6, 2013, 1 page.

Medtronic, Inc. 6996SQ Subcutaneous, Unipolar Lead with Defibrillation Coil Electrode, Technicial Manual, 22 pages.

Medtronic, Inc. 6996T Tunneling Tool, Technical Manual, 12 pages.

Pebax Product Brochure, 14 pages and can be found on-line at http://www.pebax.com/export/sites/pebax/.content/medias/downloads/literature/pebax-product-range-brochure.pdf, 14 pages.

Cigna et al., A New Technique for Substernal Colon Transposition with a Breast Dissector: Report of 39 Cases, Journal of Plastic, Reconstructive and Aesthetic Surgery, 2006:59, 4 pages.

Final Office Action from U.S. Appl. No. 14/196,298, dated Jul. 21, 2016, 15 pp.

Response to Final Office Action dated Jul. 21, 2016, from U.S. Appl. No. 14/196,298, filed Sep. 21, 2016, 11 pp.

Advisory Action from U.S. Appl. No. 14/196,298, dated Oct. 18, 2016, 5 pp.

Response to Final Office Action dated Jul. 21, 2016 and Advisory Action dated Oct. 18, 2016, from U.S. Appl. No. 14/196,298, filed Nov. 16, 14 pp.

* cited by examiner

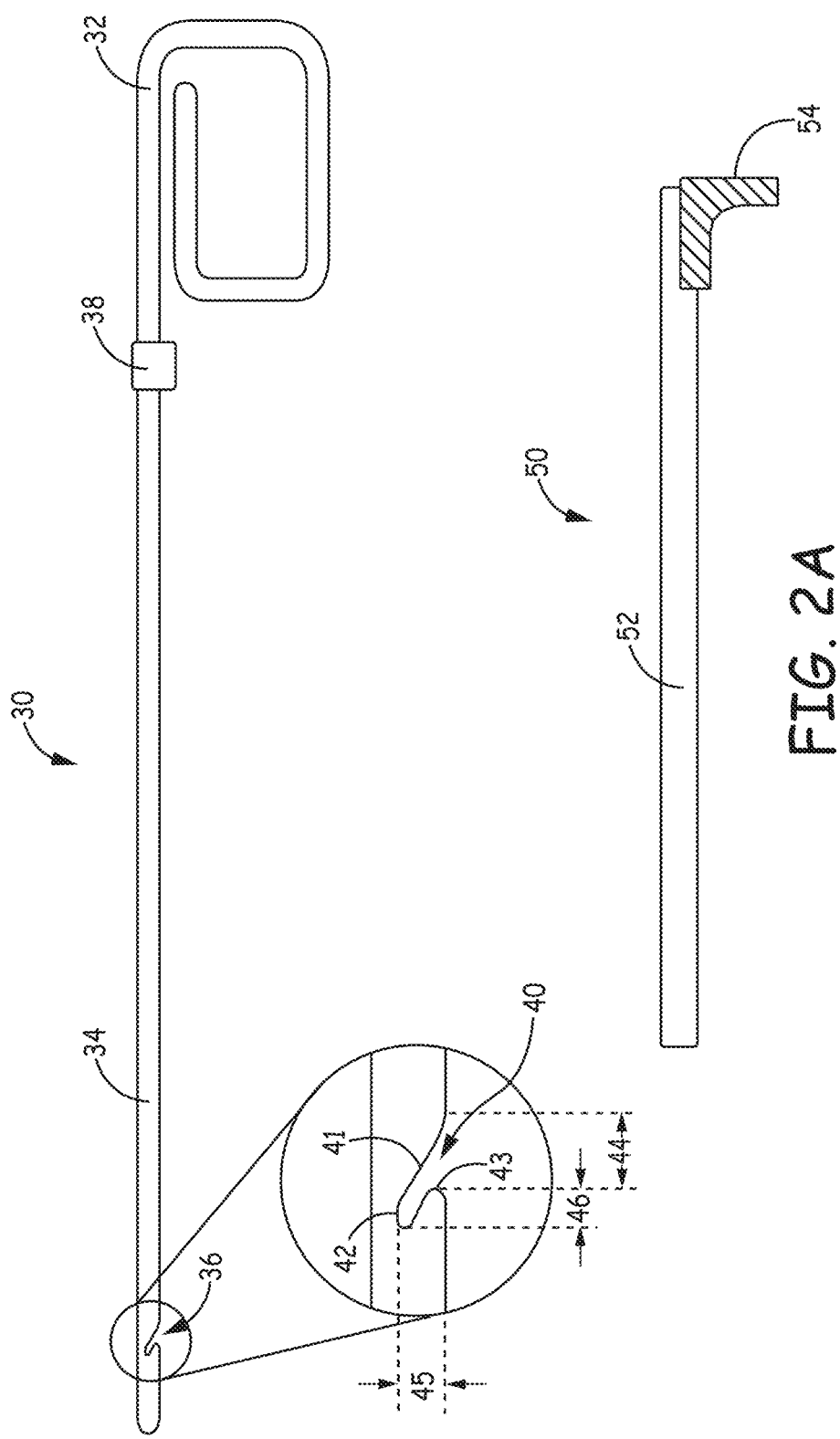

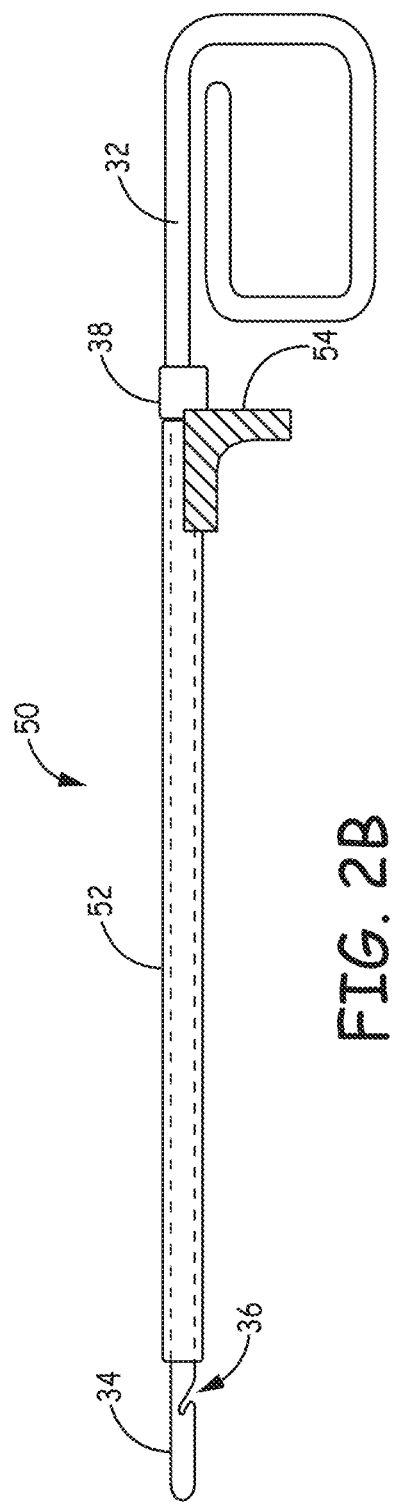

SECTION B-B'

SECTION C-C'

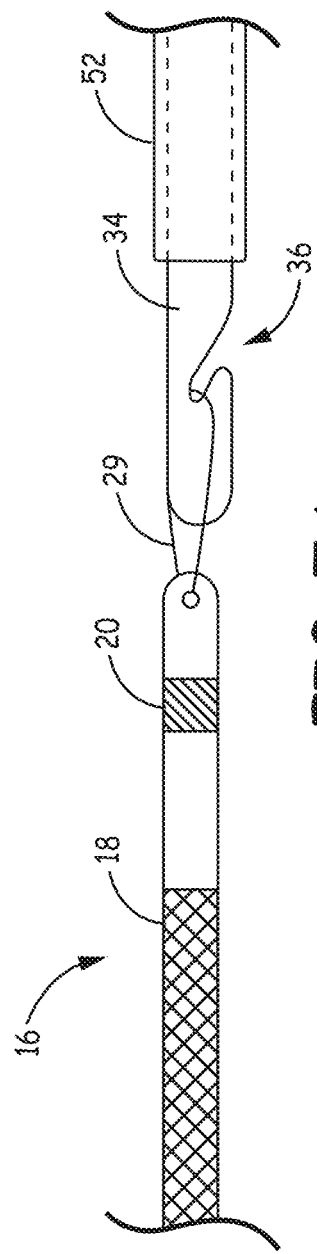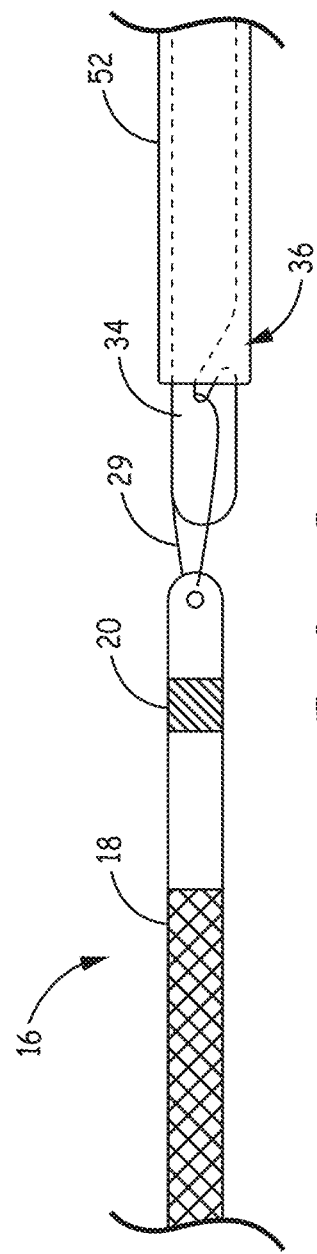

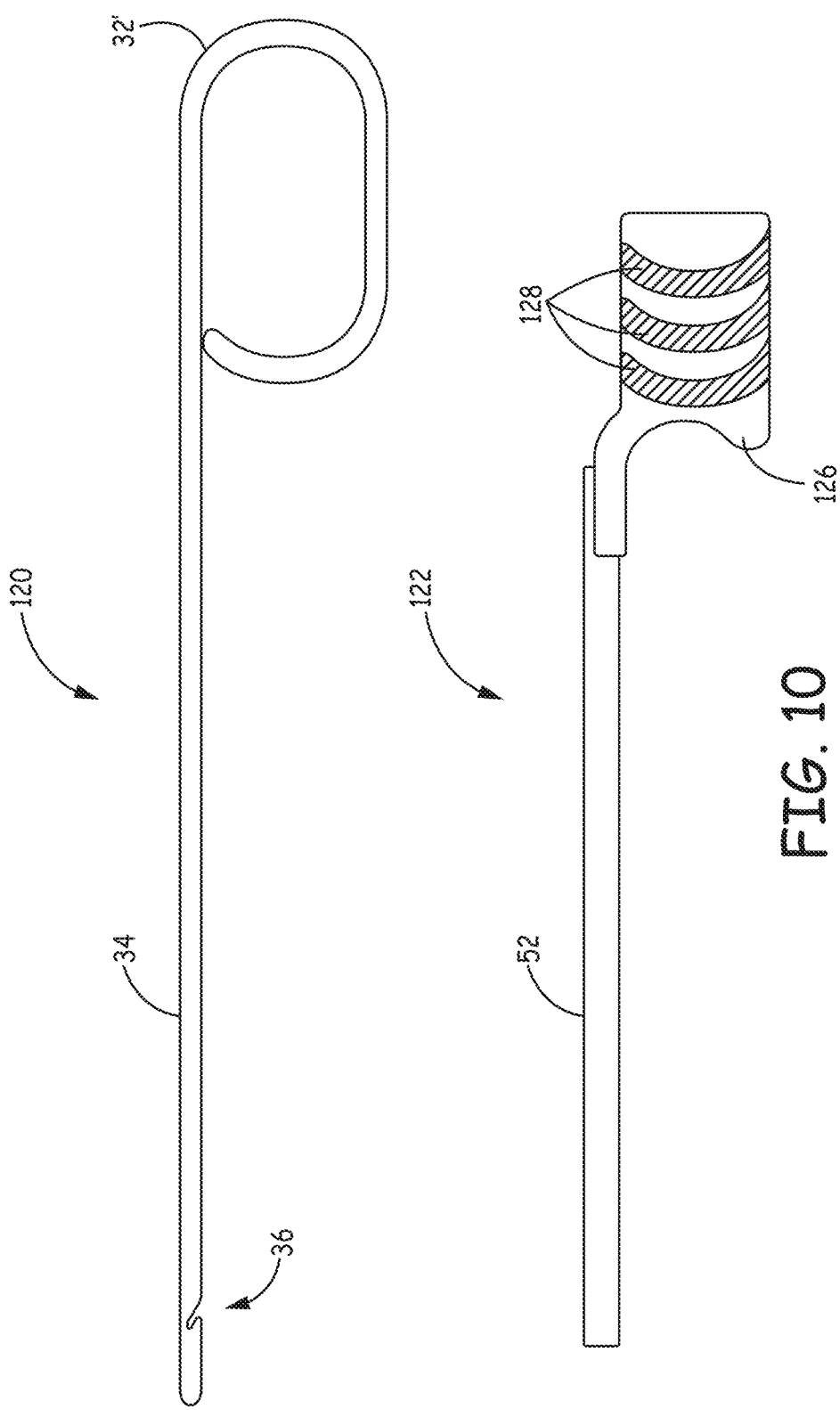

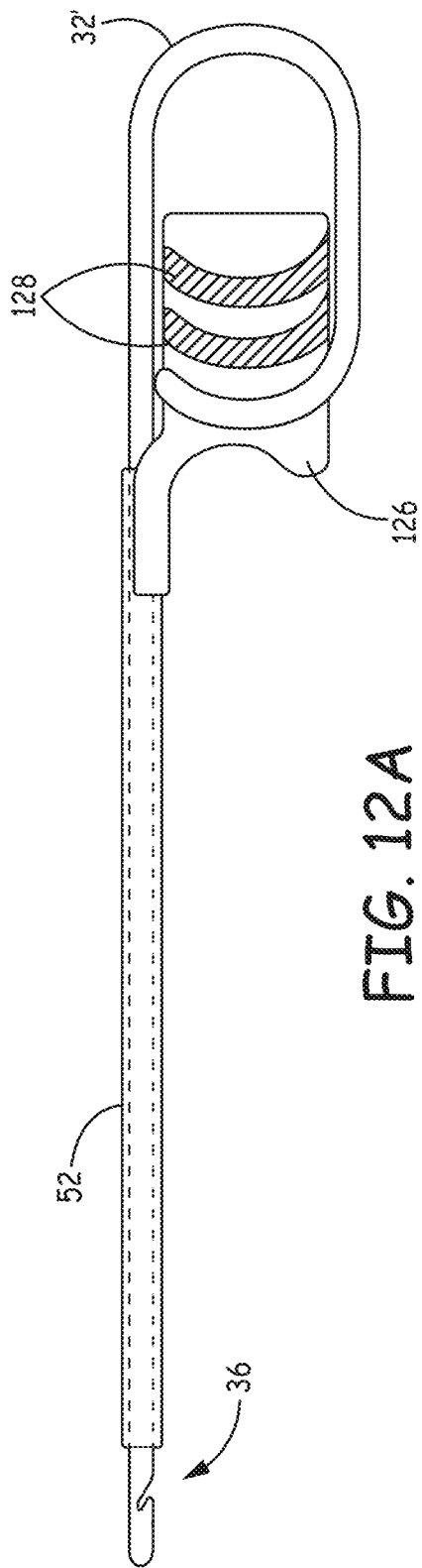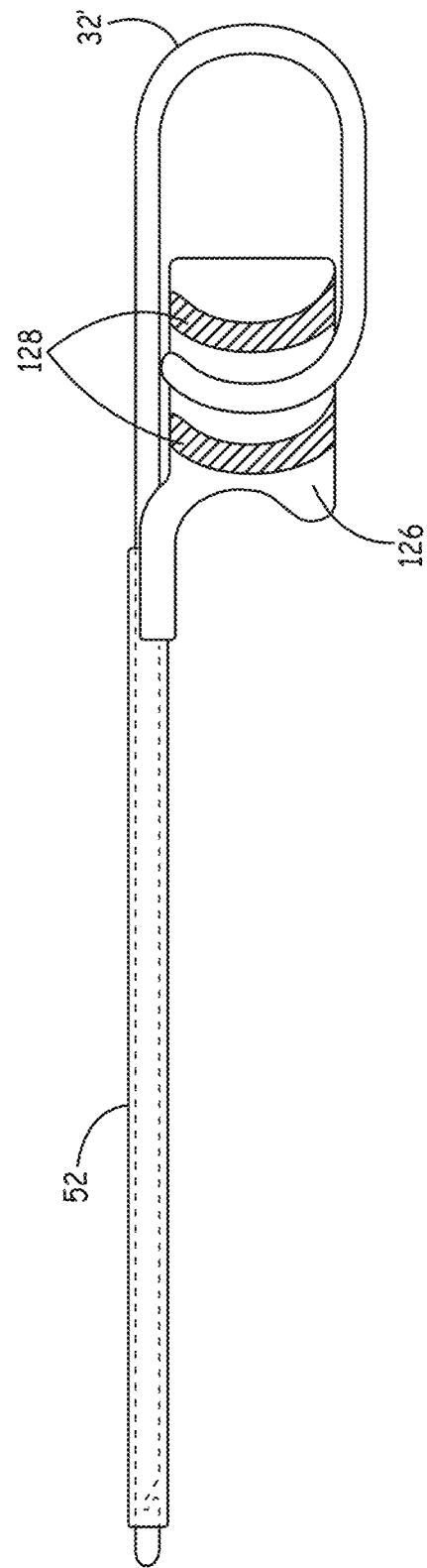

SECTION D-D'

IMPLANT TOOLS WITH ATTACHMENT FEATURE AND MULTI-POSITIONAL SHEATH AND IMPLANT TECHNIQUES UTILIZING SUCH TOOLS

This application claims the benefit of U.S. Provisional Application No. 61/903,139, filed on Nov. 12, 2013, the content of which is incorporated herein by reference in its entirety.

TECHNICAL FIELD

The present disclosure relates to implant tools and techniques for implanting medical leads or other implantable components in extravascular locations.

BACKGROUND

Implantable cardiac defibrillator (ICD) systems are used to deliver high energy electrical pulses or shocks to a patient's heart to terminate life threatening arrhythmias, such ventricular fibrillation. Traditional ICD systems include a housing that encloses a pulse generator and other electronics of the ICD and is implanted subcutaneously in the chest of the patient. The housing is connected to one or more implantable medical electrical leads that are implanted within the heart.

Traditional ICD systems that utilize transvenous leads may not be the preferable ICD system for all patients. For example, some patients with difficult vascular access precludes placement of transvenous leads. As another example, children and other younger patients may also candidates for non-transvenous ICD systems. Moreover, transvenous leads may become fibrosed in the heart over time, making lead revision and extraction procedures challenging.

A subcutaneous ICD system may be preferred for these patients. A subcutaneous ICD system includes a lead (or leads) that are implanted subcutaneously in the patient, i.e., between the skin and the ribs and/or sternum of the patient. As such, the subcutaneous ICD may eliminate the need to transvenous leads within the heart.

SUMMARY

This disclosure provides implant tools and techniques for implantation of a medical lead, catheter or other component, in extravascular locations including subcutaneous locations. In one example, this disclosure provides an implant tool for implanting a medical lead. The implant tool comprises a rod and a sheath configured to be placed on the rod. The rod includes a handle, a shaft having a proximal end adjacent to the handle and a distal end, and an attachment feature toward the distal end of the shaft, the attachment feature configured to couple to the medical lead. The sheath includes a body having proximal end and a distal end, and further wherein the sheath is configured to be placed in multiple positions along the rod including a first position in which the sheath does not interact with the attachment feature and second position in which the sheath does interact with the attachment feature.

In another example, this disclosure provides a method for implanting a medical electrical lead using a rod having a handle, a shaft having a proximal end adjacent to the handle and a distal end, and an attachment feature toward the distal end of the shaft, the attachment feature configured to couple to the medical lead, and a sheath configured to be placed on the shaft of the rod, the sheath having body defining a channel, the medical electrical lead having a proximal end including a connector mechanism configured to connect to an implantable medical device and a distal end including one or more electrodes.

The method comprises creating a first incision at a first location on a torso of a patient, creating a second incision at a second location on the torso of the patient, introducing the rod, with the sheath placed on the rod at a first position in which the sheath does not interact with the attachment feature of the rod, into the patient via the first incision, advancing the rod from the first incision to the second incision to create a first path between the first incision and the second incision, attaching an attachment feature of the medical electrical lead to the attachment feature of the rod, advancing the sheath to a second position in which the sheath does interact with the attachment feature of the rod after attaching the attachment feature of the medical electrical lead to the attachment feature of the rod, withdrawing the rod from the patient to pull the medical electrical lead along the path between the first incision to the second incision, retracting the sheath to the first position such that the sheath no longer interacts with the attachment feature of the rod, and removing the attachment feature of the medical electrical lead from the attachment feature of the rod.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF DRAWINGS

FIGS. 2A and 2B are conceptual drawings illustrating an example extravascular implant tool.

FIGS. 7A and 7B illustrate a distal end of an implant tool being attached to an implantable medical lead.

FIG. 10 illustrates an example of an implant tool that includes a rod and a sheath having a multi-positional handle.

FIGS. 12A and 12B illustrate the placement of the sheath having a multi-positional handle in two positions on the rod of the implant tool of FIG. 10.

DETAILED DESCRIPTION

Figure 1:
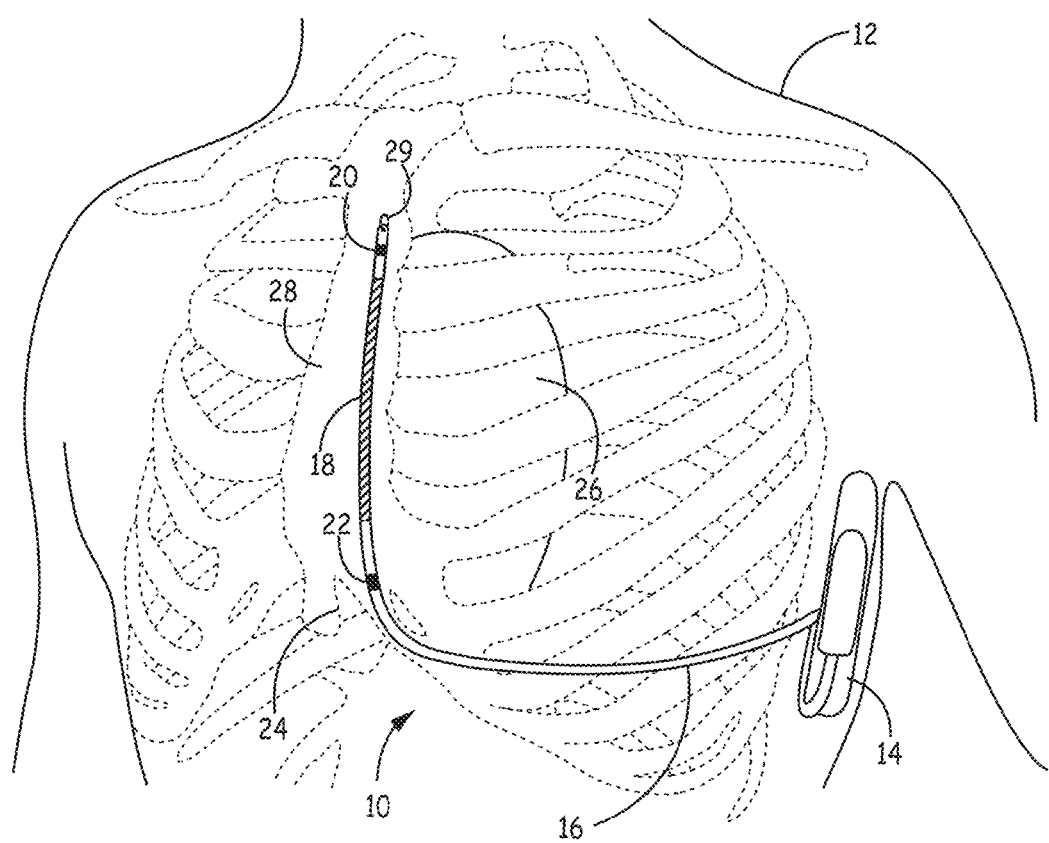
FIG. 1 is a conceptual diagram of a patient implanted with an example extravascular cardiac defibrillation system.

FIG. 1 is a conceptual diagram illustrating a patient 12 implanted with an example extravascular cardiac defibrillation system 10. In the example illustrated in FIG. 1, extravascular cardiac defibrillation system 10 is an implanted subcutaneous defibrillation system. However, the implant tools and techniques of this disclosure may also be utilized with other extravascular implanted cardiac defibrillation systems, such as a cardiac defibrillation system having a lead implanted at least partially in a substernal or submuscular location. Additionally, the implant tools and techniques of this disclosure may also be utilized with other implantable cardiac systems, such as implantable cardioverter defibrillator systems, implantable cardiac resynchronization therapy (CRT) systems (e.g., CRT-P or CRT-D systems), implantable pacing systems, other implantable cardiac systems that include combinations of the cardiac systems above. Likewise the techniques may be used in non-cardiac implantable systems, including in, implantable neurostimulation systems, drug delivery systems or other systems in which leads, catheters or other components are implanted at extravascular locations within patient 12. This disclosure, however, is described in the context of an implantable extravascular cardiac defibrillation system for purposes of illustration.

Extravascular cardiac defibrillation system 10 includes an implantable cardiac defibrillator (ICD) 14 connected to at least one implantable cardiac defibrillation lead 16. ICD 14 of FIG. 1 is implanted subcutaneously on the left side of patient 12. Defibrillation lead 16, which is connected to ICD 14, extends medially from ICD 14 toward sternum 28 and xiphoid process 24 of patient 12. At a location near xiphoid process 24 defibrillation lead 16 bends or turns and extends subcutaneously superior, substantially parallel to sternum 28. In the example illustrated in FIG. 1, defibrillation lead 16 is implanted such that lead 16 is offset laterally to the left side of the body of sternum 28 (i.e., towards the left side of patient 12).

Defibrillation lead 16 is placed along sternum 28 such that a therapy vector between defibrillation electrode 18 and a second electrode (such as a housing or can electrode of ICD 14 or an electrode placed on a second lead) is substantially across the ventricle of heart 26. The therapy vector may, in one example, be viewed as a line that extends from a point on the defibrillation electrode 18 to a point on the housing or can electrode of ICD 14. In another example, defibrillation lead 16 may be placed along sternum 28 such that a therapy vector between defibrillation electrode 18 and a housing or can electrode of ICD 14 (or other electrode) is substantially across an atrium of heart 26. In this case, extravascular ICD system 10 may be used to provide atrial therapies, such as therapies to treat atrial fibrillation.

The embodiment illustrated in FIG. 1 is an example configuration of an extravascular cardiac defibrillation system 10 and should not be considered limiting of the techniques described herein. For example, although illustrated as being offset laterally from the midline of sternum 28 in the example of FIG. 1, defibrillation lead 16 may be implanted such that lead 16 is offset to the right of sternum 28 or over sternum 28. Additionally, defibrillation lead 16 may be implanted such that it is not substantially parallel to sternum 28, but instead offset from sternum 28 at an angle (e.g., angled lateral from sternum 28 at either the proximal or distal end). As another example, the distal end of defibrillation lead 16 may be positioned near the second or third rib of patient 12. However, the distal end of defibrillation lead 16 may be positioned further superior or inferior depending on the location of ICD 14, location of electrodes 18, 20, and 22, or other factors.

Although ICD 14 is illustrated as being implanted near a midaxillary line of patient 12, ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 would follow a different path, e.g., across the upper chest area and inferior along sternum 28. When the ICD 14 is implanted in the pectoral region, the extravascular ICD system may include a second lead including a defibrillation electrode that extends along the left side of the patient such that the defibrillation electrode of the second lead is located along the left side of the patient to function as an anode or cathode of the therapy vector of such an ICD system.

ICD 14 includes a housing that forms a hermetic seal that protects components within ICD 14. The housing of ICD 14 may be formed of a conductive material, such as titanium, titanium alloy, or other biocompatible conductive material or a combination of conductive and non-conductive materials. In some instances, the housing of ICD 14 functions as an electrode (sometimes referred to as a housing electrode or can electrode) that is used in combination with one of electrodes 18, 20, or 22 to deliver a therapy to heart 26 or to sense electrical activity of heart 26. ICD 14 may also include a connector assembly (sometimes referred to as a connector block or header) that includes electrical feedthroughs through which electrical connections are made between conductors within defibrillation lead 16 and electronic components included within the housing. The housing may enclose one or more components, including processors, memories, transmitters, receivers, sensors, sensing circuitry, therapy circuitry and other appropriate components (often referred to herein as modules).

Defibrillation lead 16 includes a lead body having a proximal end that includes a connector configured to connect to ICD 14 and a distal end that includes one or more electrodes 18, 20, and 22. The lead body of defibrillation lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions. Although defibrillation lead 16 is illustrated as including three electrodes 18, 20 and 22, defibrillation lead 16 may include more or fewer electrodes.

Defibrillation lead 16 includes one or more elongated electrical conductors (not illustrated) that extend within the lead body from the connector on the proximal end of defibrillation lead 16 to electrodes 18, 20 and 22. In other words, each of the one or more elongated electrical conductors contained within the lead body of defibrillation lead 16 may engage with respective ones of electrodes 18, 20 and 22. When the connector at the proximal end of defibrillation lead 16 is connected to ICD 14, the respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 18, 20 and 22 and transmit sensed electrical signals from one or more of electrodes 18, 20 and 22 to the sensing module within ICD 14.

ICD 14 may sense electrical activity of heart 26 via one or more sensing vectors that include combinations of electrodes 20 and 22 and a housing or can electrode of ICD 14. For example, ICD 14 may obtain electrical signals sensed using a sensing vector between electrodes 20 and 22, obtain electrical signals sensed using a sensing vector between electrode 20 and the conductive housing or can electrode of ICD 14, obtain electrical signals sensed using a sensing vector between electrode 22 and the conductive housing or can electrode of ICD 14, or a combination thereof. In some instances, ICD 14 may even sense cardiac electrical signals using a sensing vector that includes defibrillation electrode 18, such as a sensing vector between defibrillation electrode 18 and one of electrodes 20 or 22, or a sensing vector between defibrillation electrode 18 and the housing or can electrode of ICD 14.

ICD may analyze the sensed electrical signals to detect tachycardia, such as ventricular tachycardia or ventricular fibrillation, and in response to detecting tachycardia may generate and deliver an electrical therapy to heart 26. For example, ICD 14 may deliver one or more defibrillation shocks via a therapy vector that includes defibrillation electrode 18 of defibrillation lead 16 and the housing/can electrode. Defibrillation electrode 18 may, for example, be an elongated coil electrode or other type of electrode. In some instances, ICD 14 may deliver one or more pacing therapies prior to or after delivery of the defibrillation shock, such as anti-tachycardia pacing (ATP) or post shock pacing. In these instances, ICD 14 may generate and deliver pacing pulses via therapy vectors that include one or both of electrodes 20 and 22 and/or the housing/can electrode. Electrodes 20 and 22 may comprise ring electrodes, hemispherical electrodes, coil electrodes, helix electrodes, segmented electrodes, directional electrodes, or other types of electrodes, or combination thereof. Electrodes 20 and 22 may be the same type of electrodes or different types of electrodes, although in the example of FIG. 1 both electrodes 20 and 22 are illustrated as ring electrodes.

Defibrillation lead 16 may also include an attachment feature 29 at or toward the distal end of lead 16. The attachment feature 29 may be a loop, link, or other attachment feature. For example, attachment feature 29 may be a loop formed by a suture. As another example, attachment feature 29 may be a loop, link, ring of metal, coated metal or a polymer. The attachment feature 29 may be formed into any of a number of shapes with uniform or varying thickness and varying dimensions. Attachment feature 29 may be integral to the lead or may be added by the user prior to implantation. Attachment feature 29 may be useful to aid in implantation of lead 16 and/or for securing lead 16 to a desired implant location. In some instances, defibrillation lead 16 may include a fixation mechanism in addition to or instead of the attachment feature. Although defibrillation lead 16 is illustrated with an attachment feature 29, in other examples lead 16 may not include an attachment feature 29. In this case, defibrillation lead 16 may be connected to or secured to an implant tool via an interference fit as will be described in more detail herein. An interference fit, sometimes also referred to as a friction fit, is a fastening between two parts which is achieved by friction after the parts are pushed together, rather than by any other means of fastening.

Lead 16 may also include a connector at the proximal end of lead 16, such as a DF4 connector, bifurcated connector (e.g., DF-1/IS-1 connector), or other type of connector. The connector at the proximal end of lead 16 may include a terminal pin that couples to a port within the connector assembly of ICD 14. In some instances, lead 16 may include an attachment feature at the proximal end of lead 16 that may be coupled to an implant tool to aid in implantation of lead 16. In one example, a portion of the connector at the proximal end of lead 16 may be utilized as the attachment feature. In another example, the attachment feature at the proximal end of the lead may separate from the connector and may be either integral to the lead or added by the user prior to implantation.

Defibrillation lead 16 may also include a suture sleeve or other fixation mechanism (not shown) located proximal to electrode 22 that is configured to fixate lead 16 near the xiphoid process or lower sternum location. The fixation mechanism (e.g., suture sleeve or other mechanism) may be integral to the lead or may be added by the user prior to implantation.

The example illustrated in FIG. 1 is exemplary in nature and should not be considered limiting of the techniques described in this disclosure. For instance, extravascular cardiac defibrillation system 10 may include more than one lead. In one example, extravascular cardiac defibrillation system 10 may include a pacing lead in addition to defibrillation lead 16.

In the example illustrated in FIG. 1, defibrillation lead 16 is implanted subcutaneously, e.g., between the skin and the ribs and/or sternum. In other instances, defibrillation lead 16 (and/or the optional pacing lead) may be implanted at other extravascular locations. In one example, defibrillation lead 16 may be implanted at least partially in a substernal location. In such a configuration, at least a portion of defibrillation lead 16 may be placed under/below the sternum in the mediastinum and, more particularly, in the anterior mediastinum. The anterior mediastinum is bounded laterally by pleurae, posteriorly by pericardium, and anteriorly by sternum. Defibrillation lead 16 may be at least partially implanted in other extra-pericardial locations, i.e., locations in the region around, but not in direct contact with, the outer surface of heart 26. These other extra-pericardial locations may include in the mediastinum but offset from sternum 28, in the superior mediastinum, in the middle mediastinum, in the posterior mediastinum, in the sub-xiphoid or inferior xiphoid area, near the apex of the heart, or other location not in direct contact with heart 26 and not subcutaneous. In still further instances, the implant tools described herein may be utilized to implant the lead at a pericardial or epicardial location outside the heart 26. Moreover, implant tools such as those described herein may be used to implant non-cardiac leads in other locations within patient 12.

FIGS. 2A and 2B are conceptual drawings illustrating an example extravascular implant tool, which includes components for implanting a medical lead, such as lead 16 of FIG. 1, a catheter, or other implantable component. The implant tool includes a rod 30 and a sheath 50. As will be described in further detail herein, the implant tool of FIGS. 2A and 2B may be particularly useful in implanting defibrillation lead 16 in patient 12 in a subcutaneous, substernal, or other extravascular location.

Rod 30 includes a handle 32 at a proximal end of rod 30 and an elongate shaft 34 that extends from handle 32 to a distal end of rod 30. The distal end of rod 30 of elongate shaft 34 may be shaped to aid in tunneling through subcutaneous or other tissue, muscle, ligament or bodily structure. For example, the distal end of the elongate shaft 34 may be blunt, rounded, tapered, pointed or otherwise shaped to enable a user to tunnel through subcutaneous or other tissue without excess damage to surrounding tissue, piercing through the skin, or coring of the tissue. In some instances, the distal end of rod 30 may be bent or curved, which may aid in tunneling under sternum 28. In particular the bend or shape may be oriented toward the sternum and follow along the underside of the sternum to reduce the likelihood of damage to the pleural or pericardium or other structure.

Elongate shaft 34 of rod 30 is formed such that it is stiff enough to be capable of being pushed through the tissue, muscle or other structure to form a path through the body. Shaft 34 may be made of a metal, alloy, polymer, or other material or combination of materials. In some instances, such as when shaft 34 is made of metal or alloy, shaft 34 may be malleable. For example, a user of rod 30 may form shaft 34 to achieve a desired shape or bend. In this case, an implant kit may include the tool (e.g., rod 30 and sheath 50) as well as a bending tool (not illustrated in FIGS. 2A and 2B) to aid the user in forming the tool to the desired shape or with the desired bend. However, rod 30 may be formed by the user without a designated bending tool. In other instances, the implant tool may include a pre-formed or pre-shaped rod having a curve or bend toward a distal end of shaft. Alternatively, shaft 34 may not be malleable, such as when shaft 34 is formed from a polymer. Even when shaft 34 is not malleable, however, shaft 34 may be somewhat flexible while still being stiff enough to tunnel through tissue. The flexibility may allow a user to manipulate the tool slightly to control direction (e.g., steer) of the tunnel. For example, a downward or upward force applied near the distal end of handle 32 (e.g., adjacent to shaft 34) may result in shaft 34 flexing such that the distal end of shaft 34 is directed upward or downward, respectively. Similarly, a force applied in to the left or right near the distal end of handle 32 may result in shaft 34 flexing such that the distal end of shaft 34 is directed right or left, respectively.

Handle 32 of rod 30 may also be made of a metal, alloy, polymer, or other material or combination of materials. Handle 32 and elongate shaft 34 may, in some instances, be constructed of the same material. For example, rod 30 may be formed of a single, unitary piece of material, such as a molded metal or rigid polymer. In other instances, handle 32 and elongate shaft 34 may be constructed of different materials. In this case, handle 32 and shaft 34 may be formed of separate components that are attached together to form rod 30, e.g., via a two piece construction. For example, handle 32 may be made of polymer and shaft 34 may be made of metal and attached to handle 32 to form rod 30. Example metals or alloys from which handle 32 or shaft 34 may be constructed include, but are not limited to, stainless steel, titanium, titanium alloys, nickel-cobalt, and nickel-cobalt alloys. Example polymers may include, but are not limited to, acetal (e.g., DELRIN®), Polyether ether ketone (PEEK), polycarbonate, polypropylene composites, and liquid-crystal polymer (LCP).

Rod 30 also includes an attachment feature toward the distal end of elongate shaft 34. In the example illustrated in FIGS. 2A and 2B, the attachment feature is illustrated as a hook feature 36. In other instances, hook feature 36 may be located further distal along elongate shaft 34. Hook feature 36 is a mechanism by which rod 30 may attach to a medical electrical lead, e.g., via an attachment feature 29 of lead 16. For example, attachment feature 29 (e.g., suture, loop or the like) of lead 16 may be placed within hook feature 36 such that lead 16 may be pulled through a path in the tissue of patient 12 as rod 30 is withdrawn from the body of patient 12.

In the example illustrated in FIG. 2A, hook feature 36 is in-line with shaft 34. In other words, the outer diameter of shaft 34 distal to hook feature 36 is approximately the same as the outer diameter of shaft 34 proximal to hook feature 36. In other instances, however, hook feature 36 may not be in-line, in which case, the outer diameter of shaft 34 distal to hook feature 36 is smaller than the outer diameter of shaft 34 proximal to hook feature 36 or the outer diameter of shaft 34 distal to hook feature 36 is greater than the outer diameter of shaft 34 proximal to hook feature 36.

Hook feature 36 may be formed in a number of different manners. In one example, hook feature 36 may be an angled slot across a bottom portion of shaft 34 with deburred edges. As illustrated in the enlarged view of hook feature 36, shaft 34 defines a groove 40 that extends into shaft 34 and toward the distal end of shaft 34. In particular, shaft 34 includes a lead-in 41 that tapers into shaft 34 and toward a distal end of shaft 34, a bend 42 that curves to form the bowl of groove 40, and a lip 43. Lip 43 may be designed to be rounded or tapered to avoid catching on tissue or muscle when rod 30 is retracted or removed from body of patient 12. The shape of lip 43, radius of curvature of lip 43, or other characteristic of lip 43 may be selected or designed to reduce the amount of resistance hook feature 36 presents during retraction or removal of rod 30 from patient 12. The distance 44 from the most proximal portion of lip 43 to the most proximal portion of lead-in 41 may also be selected or designed to be large enough to receive attachment feature 29 of lead 16, but small enough to reduce the likelihood of catching tissue or muscle during removal of rod 30 from patient 12.

Although the attachment feature of rod 30 is illustrated as a hook 36 in FIG. 2A, the attachment feature may be formed as other features that may be used to couple to a feature on a lead to pull the lead through a subcutaneous path within patient 12. In another embodiment, the attachment feature may be a formed to receive a particular portion of a lead. For example, the attachment feature may be formed to receive a terminal pin of the connector at the proximal end of lead 16. In this case, the terminal pin of the connector of the lead may be placed within the attachment feature. Such an embodiment is described in further detail with respect to FIGS. 13A and 13B.

Groove 40 has a width 44, depth 45 and throat 46. The size of width 44, depth 45 and throat 46 of groove 40 may be designed based on the type of attachment feature 29 of lead 16 expected to be implanted using rod 30. For example, throat 46 may be much smaller such that it is just deep enough to catch a suture. Groove 40 of hook feature 36 is designed such that when rod 30 is being pulled, attachment feature 29 of lead 16 is preferentially pulled into throat 46 of groove 40.

Rod 30 may include a stop 38 toward a proximal end of rod 30. In the example illustrated in FIG. 2A, stop 38 is located at the point of transition from shaft 34 to handle 32. In other examples, however, stop 38 may be located further distal along shaft 34. In some instances, stop 38 may be moveable.

Sheath 50 includes a body 52 having a proximal end and a distal end and a handle 54 located at the proximal end of body 52. In some instances, the distal end of body 52 may be tapered to aid in tunneling. Body 52 of sheath 50 defines an inner channel. As will be described in further detail below, sheath 50 may be an open sheath as illustrated and described in further detail with respect to FIGS. 3A-E, 4A, and 4B. In the case of an open sheath, sheath 50 may include an opening along the length of body 52 and the inner channel is accessible via the opening anywhere along the length of body 52. In another example, sheath 50 may be a splittable sheath in which body 52 includes a score or other weakened portion to permit splitting of body 52, e.g., as illustrated and described in further detail with respect to FIG. 5. In yet another example, sheath 50 may be a sheath without any gap or score on body 52, in which case sheath 50 may be removed by slitting the sheath using a slitter, as illustrated and described in further detail with respect to FIG. 6.

Sheath 50 may be made of extruded or molded material. The material may include, but not limited to, a polymer, a copolymer, a thermoplastic, or other material. Example materials include, but are not limited to, polyether block amide (such as PEBAX® 72D), polyether block amide blends (PEBAX® with a Foster ProPell™ additive), polyethylene, ultra-high-molecular-weight polyethylene (UHMWPE), Polytetrafluoroethylene (PTFE), nylons (such as GRILAMID® TR55 or L25, VESTAMID® L2140, AESNO®), or the like. In some instances, sheath 50 may be made of multiple layers of different materials or may vary in materiality and durometer along the length of body 52. For example, sheath 50 may be formed of PEBAX® with a PTFE lining the inner surface of the channel. Other additives or coatings that may be applied to increase lubricity include, but are not limited to, siloxane, PTFE, and Foster ProPell™.

In some instances, rod 30 and/or sheath 50 may include markings (not shown in FIGS. 2A and 2B) that may aid the user during the implant procedure. For example, the markings may provide the user feedback regarding the distance tunneled or orientation of a shape and/or feature of rod 30. As another example, the markings may coincide with features on lead 16. The markings may, for instance, coincide with electrodes 18, 20 and 22, correspond with fixation mechanisms (such as a suture sleeve of lead 16), or other feature on lead 16. In instances in which the markings coincide with features of lead 16, the user may utilize the marking prior to beginning the procedure to place landmarks on the skin of the patient. The user could then be more confident that when the insertion tool is routed according to the landmarks that the electrodes or other lead features will be in the desired locations. The markings may be laser etched, printed, or otherwise placed on rod 30, sheath 50, or both.

FIG. 2B illustrates the implant tool formed by placing sheath 50 over rod 30. In some instances, sheath 50 may be sized such that sheath 50 fits on shaft 34 of rod 30 in such a manner that an interference fit is achieved between sheath 50 and shaft 34 of rod 30. As described above, the interference fit is achieved by friction after the parts are pushed together, rather than by any other means of fastening. The interference fit may, in some instances, be achieved by sizing and/or shaping the two mating parts so that one or the other, or both, slightly deviate in size from the nominal dimension. The interference fit may therefore be viewed as referring to the fact that one part slightly interferes with the space that the other is taking up. The tightness of the interference fit may be controlled by the amount of allowance, e.g., the planned difference from nominal size. Different allowances will result in various strengths of fit. The value of the allowance depends on which material is being used, how big the parts are, and what degree of tightness is desired.

In one example, the diameter of the inner channel formed by body 52 of sheath 50 may be equal to or slightly smaller than the outer diameter of shaft 34 of rod 30. The allowance in this case may be on the order of 1-10 thousandths of an inch. Allowances of less than 1 thousandth and greater than 10 thousands may be used, however. As such, when placed over shaft 34 of rod 30, sheath 50 slightly expands in diameter causing the interference fit. In some instances, the implant tool comprising sheath 50 disposed over rod 30 may be used to pull a lead, such as defibrillation lead 16, through a tunnel formed within tissue of patient 12. In some cases, the interference fit may be tight enough to prevent sheath 50 from being pulled off shaft 34 of rod 30 when being used to pull lead 16 through the tunnel within patient 12. However, the interference fit must also enable a user to easily place sheath 50 over shaft 34 of rod 30. Other techniques for achieving an interference fit may also be utilized. In other embodiments described herein, handle 54 of sheath 50 may be configured to retain sheath 50 in multiple positions on rod 30. This will be described in further detail with respect to FIGS. 10-13

In one embodiment, sheath 50 may have a length that is shorter than a length of shaft 34 of rod 30. In this manner, the distal end of shaft 34 of rod 30 extends beyond the distal end of sheath 50. In the embodiment illustrated in FIG. 2B, body 52 of sheath 50 is short enough such that when handle 54 of sheath 50 abuts against stop 38 of rod 30, hook feature 36 of the distal end of rod 30 extends beyond the distal end of sheath 50.

Rod 30 and sheath 50 may be sized based on the desired application. Rod 30 may have diameter that is slightly larger than the diameter of the lead for which it will be used to implant, e.g., lead 16. In one example, rod 30 may have a diameter that is approximately one-half of a French larger than the diameter of lead 16. The implant tool may be used to deliver leads of various sizes, such as 3-11 French leads (e.g., 1-3.7 mm leads). Sheath 50 may be sized to have an inner diameter (e.g., the diameter of the inner surface of sheath 50) that is equal to or slightly less than the diameter of rod 30. In some instances the size of sheath 50 may also be selected based on the diameter of the lead for which it will be used to implant. For example, sheath 50 may be sized such that the inner diameter is slightly larger than the diameter of the lead.

FIGS. 3A-3E illustrate various views of an open sheath 60. Sheath 60 can include one or more of the structure and/or functionality of sheath 50 (and vice versa). Repetitive description of like numbered elements in other embodiments is omitted for sake of brevity. Sheath 60 may, in one example, be used in conjunction with rod 30 in place of sheath 50.

3A illustrates a front view of sheath 60. 3B illustrates a top view of sheath 60. As illustrated in the top view of FIG. 3B, sheath 60 includes an opening 62 that extends the entire length of body 62 from the distal end to the proximal end and through handle 61. As illustrated in FIG. 3B, channel 64 is accessible via opening 62 anywhere along the length of body 63 from the proximal end to the distal end. In the example illustrated in FIG. 3B, opening 62 follows a substantially straight path from the distal end of body 63 of sheath 60 to the proximal end of body 63 of sheath 60. In alternative configurations, however, opening 62 may follow other paths from the distal end of body 63 to the proximal end of body 63, such as a spiral path or a meandering path.

Figure 3A:
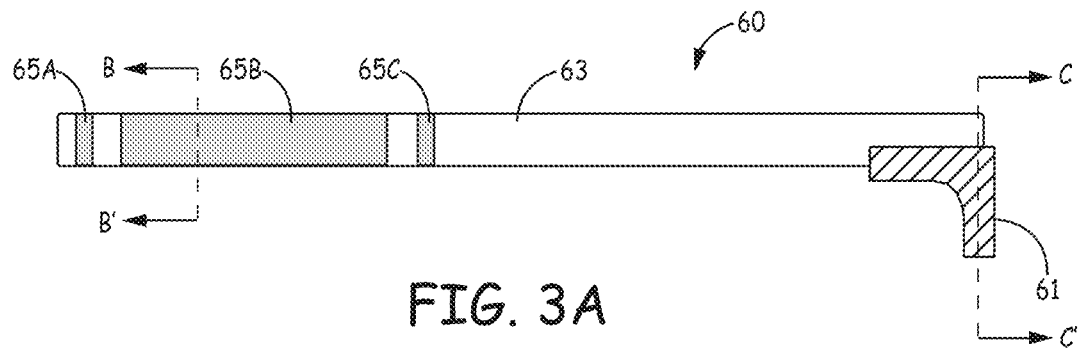
FIGS. 3A-3E are conceptual drawings illustrating various views of an example open sheath of FIGS. 2A and 2B in further detail.
Figure 3B:
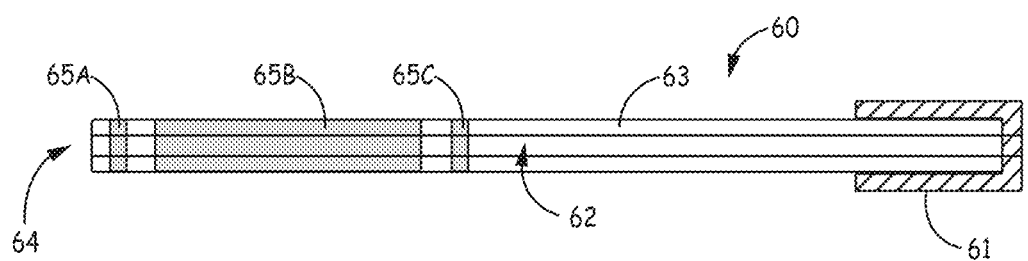

FIGS. 3A and 3B illustrate sheath 60 having markings 65A-C (collectively, markings 65) that may aid the user during the implant procedure. In the example, illustrated in FIGS. 3A and 3B, markings 65A-C coincide with electrodes 18, 20 and 22, respectively, of lead 16 when the distal end of lead 16 is aligned with the distal end of sheath 60. In other instances, markings 65 may correspond with other features of lead 16, such as fixation mechanisms (e.g., an anchor sleeve of lead 16). In instances in which the markings coincide with features of lead 16, the user may utilize the marking prior to beginning the procedure to place landmarks on the skin of patient 12. For example, prior to creating incisions or prior to tunneling, the user may place the implant tool on the skin of patient 12 such that markings 65 coinciding with the electrodes are located at a desired location, e.g., to achieve a desired therapy vector. The user may then place landmarks on the skin of patient 12, such as landmarks corresponding with a desired end point of a tunnel or a desired tunneling path that places the features (e.g., electrodes 18, 20, and 22) of lead 16 at the desired location. In this manner, the user may use the markings on the implant tool to be more confident that when rod 30 is routed according to the landmarks on the skin that the electrodes or other lead features will be in the desired locations. The markings 65 may additionally or alternatively provide the user feedback regarding the distance tunneled or orientation of a distal feature of rod 30 (e.g., an orientation of a bend or curve at the distal end), in which case the markings may be located toward the proximal end of sheath 60. Markings 65 may be laser etched, printed, or otherwise placed on sheath 60. Additionally or alternatively, similar markings may be made on rod 30. In other instances, sheath 60 and rod 30 may not include any markings.

Figure 3C:
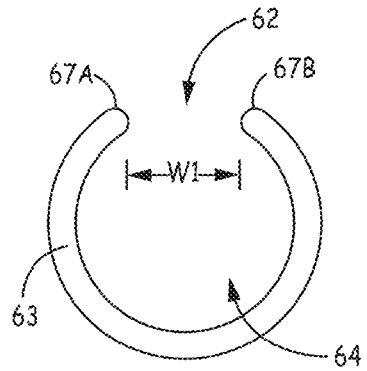

FIG. 3C illustrates a cross-sectional view of the distal end of sheath 60 taken from B-B'. As illustrated in FIG. 3C, body 63 is C-shaped such that opening 62 defines a gap between end 67A and end 67B of body 63. In other words, a gap exists between ends 67A and 67B along the circumference or cross-section of body 63. Opening 62 may have a width "W1". Body 63 defines a channel 64 that extends along the length of body 63 from the distal end to the proximal end and through handle 61. In this case, channel 64 is a C-shaped channel, but the shape of channel 64 may vary depending on the cross-sectional shape of body 63.

Figure 3D:
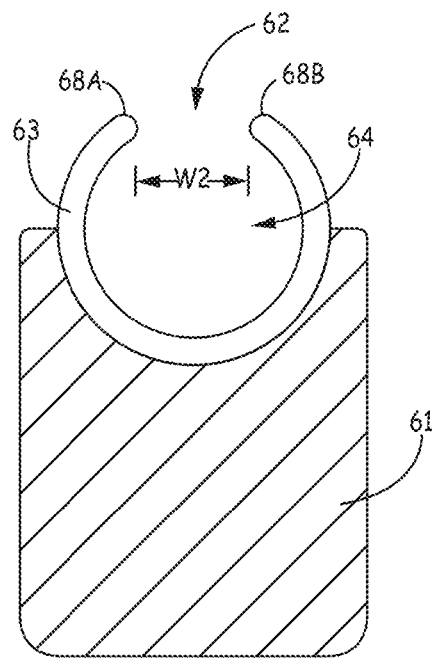

FIG. 3D illustrates a cross-sectional view of the proximal end of sheath 60 taken from C-C'. As illustrated in FIG. 3D, body 63 has a similar C-shaped configuration such that the opening 62 defines a gap between end 68A and end 68B of body 63 such that channel 64 is accessible via opening 62. Opening 62 at the proximal end of sheath 60 has a width "W2". The proximal end of sheath 60 resides within a groove of handle 61 such that handle 61 extends partially around the outer circumference of body 63. Handle 61 extends radially away from body 63 to provide a user of insertion tool the ability to grasp handle 61 to remove a lead from channel 64 or place sheath 60 over rod 30.

The widths W1 and W2 defined by opening 62 may vary in size. In some instances, widths W1 and W2 are substantially the same size. For example, the width formed by opening 62 may be substantially the same width along the length of body 63. In another example, the width formed by opening 62 at the proximal and distal end may be the same, but the width toward a middle of body 63 of sheath 60 may be narrower. In other instances, widths W1 and W2 may have different widths such that the width formed by opening 62 may vary along the length of sheath 60. For example, width W1 at the distal end of sheath 60 may be narrower than width W2 at the proximal end of sheath 60 such that lead 16 may be more easily inserted within channel 64. As another example, the width W1 at the distal end of sheath 60 may be wider than width W2 at the proximal end of sheath 60.

Figure 3E:
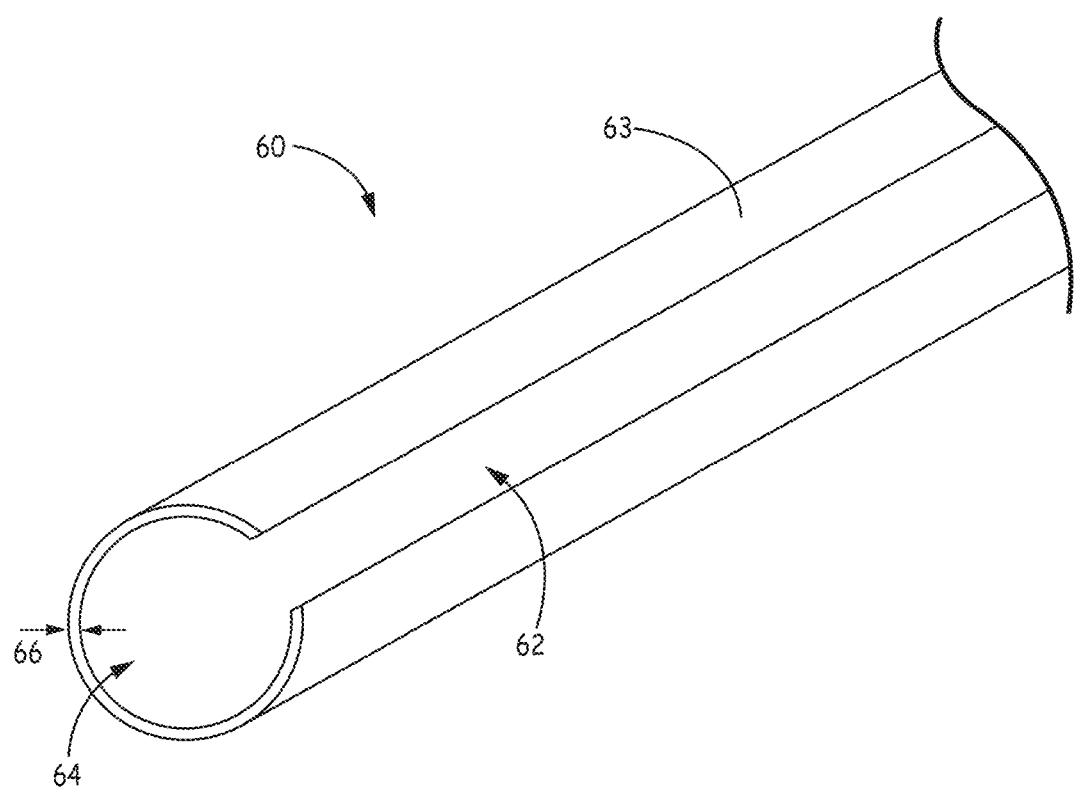

FIG. 3E illustrates an angled view of the distal end of sheath 60. Body 63 of sheath 60 forms inner channel 64 that extends the entire length of body 63 and through handle 61. Sheath 60 may be sized such that inner channel 64 is equal to or slightly less than the outer diameter of rod 30 yet allows for passage of a lead, such as defibrillation lead 16 of FIG. 1 when sheath 60 is not disposed on shaft 34 of rod 30. Thus, the diameter of body 63 defining inner channel 64 may be sized to be equal to or slightly smaller than the outer diameter of shaft 34 of rod 30 such that when placed on rod 30 an interference fit is achieved between shaft 34 and sheath 60. Sheath 60 may be formed to have a thickness 69 that may vary depending on the type of material used to form sheath 60, the desired rigidity of sheath 60, or the like. Sheath 60 should be rigid enough to not crumple, wrinkle, crease, or crush while being tunneled through tissue of patient 12.

Figure 4A:
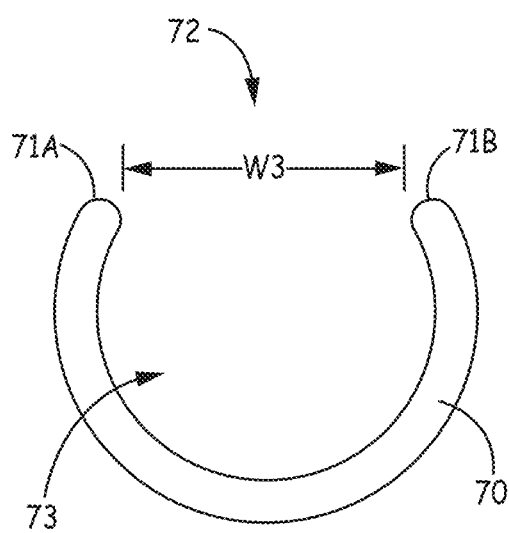
FIGS. 4A and 4B illustrate example alternative cross-sections of a distal end of an open sheath.
Figure 4B:
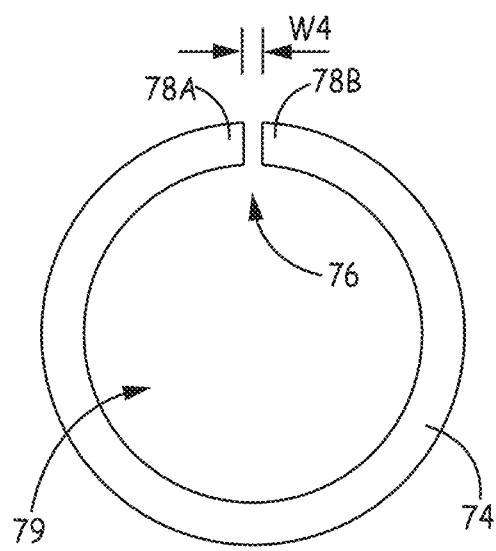

Opening 62 may vary in size depending upon the desired application. Opening 62 may be less than the diameter of lead 16. In one example, opening 62 may be approximately 10% less than the diameter of lead 16. However, in other examples, opening 62 may be less than 10% of the diameter of lead 16 or more than 10% of the diameter of lead 16. Opening 62 may be larger or smaller than illustrated in FIGS. 3A-3E. FIGS. 4A and 4B illustrate two example alternative cross-sections of a distal end of an open sheath.

FIG. 4A illustrates a cross-sectional view of the distal end of an example body 70 of a sheath. Body 70 may correspond to body 63 of sheath 60 of FIGS. 2 and 3 or any other sheath described herein and may include one or more of the structure and/or functionality of body 63 of sheath 60. As illustrated in FIG. 4A, body 70 has an opening 72 that defines a gap between ends 71A and 71B. Body 70 may be generally viewed as being c-shaped, horse-shoe shaped or semi-circle shaped defining a similarly shaped channel 73. Opening 72 may have a width "W3" is equal to or slightly smaller than the diameter of lead 16. Opening 72 has a width W3 that is larger in size than widths W1 and W2 of opening 62 of FIGS. 3A-3E.

FIG. 4B illustrates a cross-sectional view of another example body 74 of a sheath. Body 74 may correspond to body 63 of sheath 60 or any other sheath described herein and may include one or more of the structure and/or functionality of body 63 of sheath 60. As illustrated in FIG. 4C, body 74 extends around substantially the entire circumference such that opening 76 defines only a small gap between the ends 78A and 78B of body 74. As such, channel 79 formed by body 74 is essentially a lumen. Opening 72 may have a width "W4", which is smaller than the widths W1 and W2 of opening 62 of FIGS. 3A-3E. Although opening 76 is illustrated as having a small width W4, in other embodiments, ends 78A and 78B of body 74 may be in contact with one another or overlapping such that the opening does not define a gap, but ends 78A and 78B are not mechanically coupled and are moveable relative to one another. Openings 62, 72, and 77 may be formed via cutting, slitting, molding, extruding, or otherwise forming the openings.

Open sheath 60 (or other open sheaths described herein) may provide a multi-use sheath that may be reused more than once during a procedure by simply putting the sheath 60 back over rod 30. Sheath 60 may thus be used to route lead 16 through more than one tunnel through tissue of the patient or if the lead needs to be repositioned during the procedure. As another example, sheath 60 may permit the user to access channel 64 formed by opening 62 anywhere along sheath 60. This may be a desirable feature as every patient may have paths of different lengths and the user may access channel 64 of sheath 60 in close proximity to the incision site. Sheath 60 may also provide handling advantages in that it may be removed with only two hands, e.g., one to hold lead and the other to hold handle of sheath 60.

Figure 5:
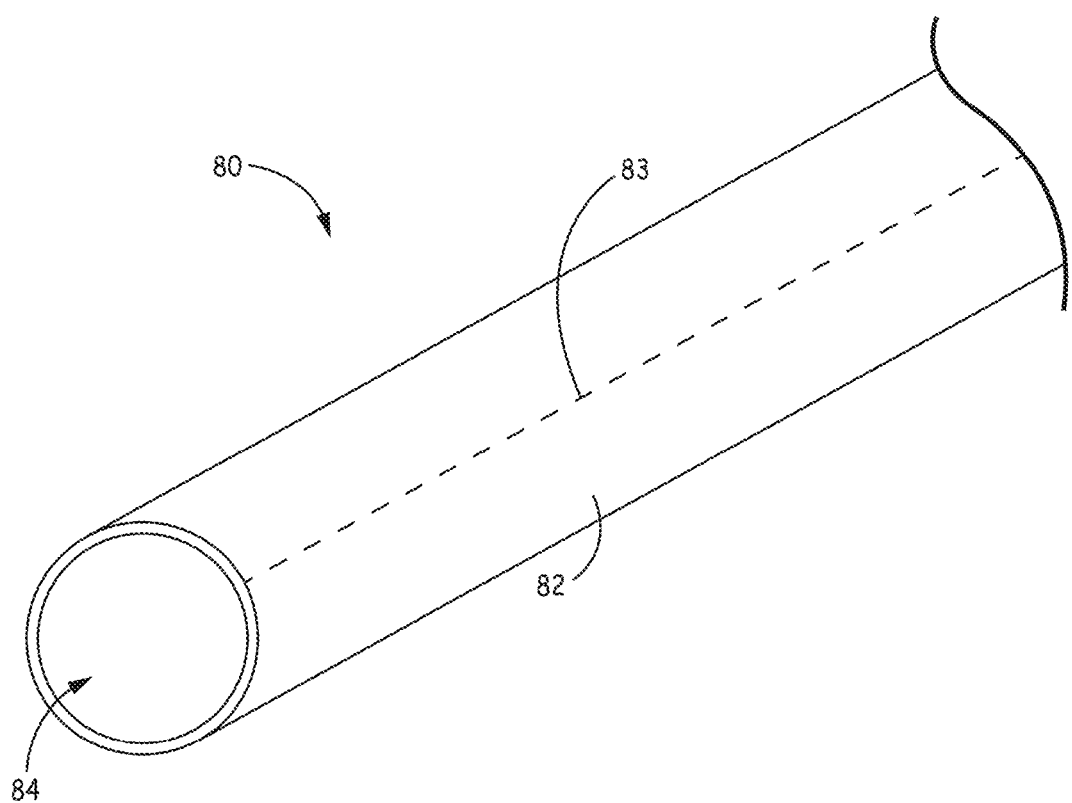
FIG. 5 illustrates an angled view of a distal end of an example splittable sheath.

FIG. 5 illustrates an angled view of the distal end of an example sheath 80. Sheath 80 can include one or more of the structure and/or functionality of sheath 50 or 60 (and vice versa). Repetitive description of like numbered elements in other embodiments is omitted for sake of brevity. Sheath 80 may, in one example, be used in conjunction with rod 30 of FIGS. 2A and 2B.

Sheath 80 may be substantially similar to sheath 60 of FIG. 3 except that body 82 of sheath 80 does not include an opening 62. Instead, body 82 forms a channel 84 that is a lumen accessible via the proximal end or distal end of body 82. Body 82 of sheath 80 includes a score 83 that extends along substantially the entire length along body 82 from the distal end of body 82 of sheath 80 to the proximal end of body 82 proximate a handle of the sheath. Unlike opening 62 of sheath 60, score line 83 does not create a gap or space along the circumference or cross-section of sheath 80 that extends along the length of body 82. Instead, score line 83 provides a weakened portion of body 82 that is more susceptible to breaking or tearing than the remainder of body 82. When a user interacts with handle at the proximal end of body 82, e.g., by applying oppositely directed forces to two sides of the handle, body 82 of sheath 80 tears or breaks along score line 83 to permit removal of lead 16 from within channel 84.

Score line 83 may follow a substantially straight path from the distal end of body 82 of sheath 80 to the proximal end of body 82 of sheath 80. Alternatively, score 83 may follow other paths from the distal end of body 82 to the proximal end of body 82, such as a spiral path, a meandering path, or other path. Although illustrated as a score line 83, body 82 of sheath 80 may include weakened portions formed using other techniques. For example, body 82 may be formed such that it is substantially thinner along the path to for a weakened portion. Moreover, although a single score line 83 is illustrated in the example of FIG. 5, body 82 of sheath 80 may include more than one score line 83. For example, body 82 of sheath 80 may include a pair of score lines 83 that are spaced 180 degrees circumferentially apart on body 82 of sheath 80.

Figure 6:
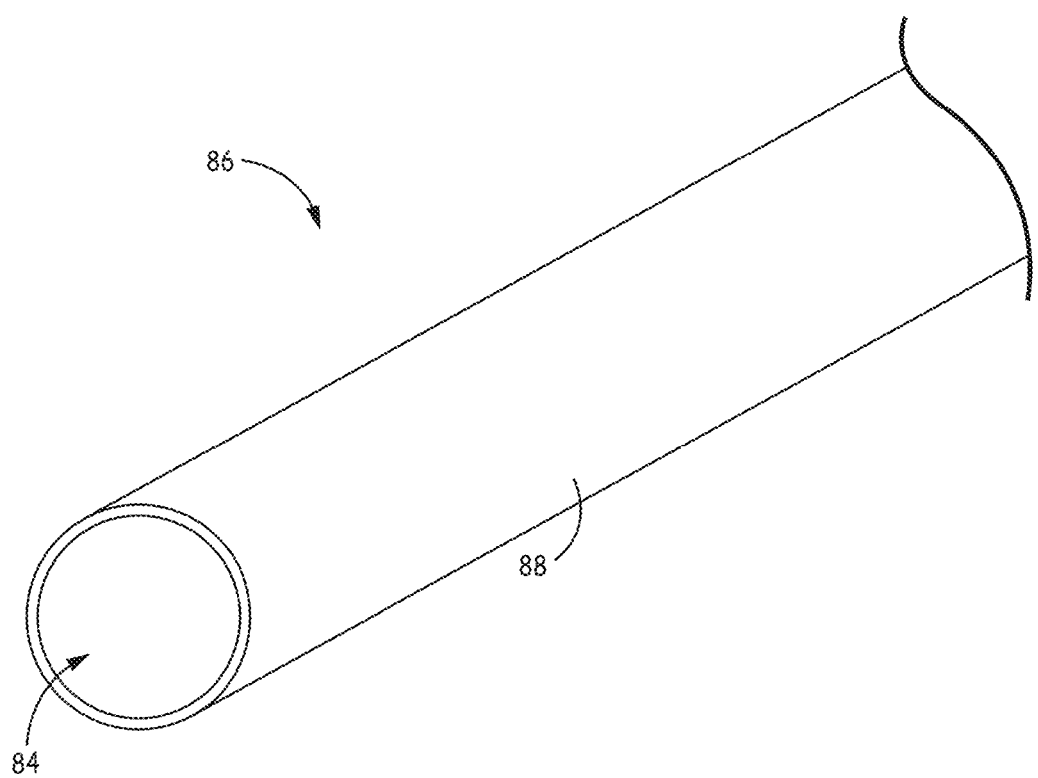
FIG. 6 illustrates an angled view of a distal end of an example slittable sheath.

FIG. 6 illustrates an angled view of the distal end of an example sheath 86. Sheath 86 can include one or more of the structure and/or functionality of sheath 50, 60, or 80 (and vice versa). Repetitive description of like numbered elements in other embodiments is omitted for sake of brevity. Sheath 86 may, in one example, be used in conjunction with rod 30 of FIGS. 2A and 2B. Sheath 86 may be substantially similar to sheath 60 of FIG. 3 or sheath 80 of FIG. 5 except that body 88 does not include an opening 62 or a score line 83, respectively. Instead, body 88 of sheath 86 may be slit open to remove lead 16 using a slitter or other means.

FIGS. 7A and 7B illustrate a distal end of the implant tool, such as the implant tool formed by rod 30 and one of sheaths 50, 60, 80, or 86, being attached to a lead, such as defibrillation lead 16. Although described in the context of sheath 50, any of the sheaths described herein may be used in place of sheath 50. As illustrated in FIG. 7A, attachment feature 29 of lead 16 is placed within hook feature 36. In some instances, sheath 50 may be pushed or slid toward the distal end of rod 30 until body 52 of sheath 50 extends over the opening of hook feature 36 thereby enclosing attachment feature 29 within hook feature 36, as illustrated in FIG. 7B.

The position of sheath 50 may be adjusted on rod 30 to cover the opening of groove 60 of hook feature 36 may ensure that attachment feature 29 of lead 16 does not exit from groove 60 while being pulled through the path formed in the tissue. Additionally, extending sheath 50 to cover the opening of groove 60 may prevent lip 43 or other portion of hook feature 36 from catching on tissue or muscle when rod 30 pulled back through the path formed in the tissue. After lead 16 is pulled through the path in the tissue, the position of sheath 50 may again be adjusted, e.g., by pulling or sliding sheath 50 toward handle 32 of rod 30 such that body 52 no longer extends over the opening of groove 60 and attachment feature 29 of lead 16 may be removed from groove 60. In this manner, sheath 50 may be placed in multiple positions on rod 30.

When positioned over the opening of groove 60, sheath 50 may be held in place on shaft 34 of rod 30 by the interference fit described above. In other instances, rod 30 or sheath 50 may designed to include a mechanism to hold sheath 50 in place when positioned over the opening of groove 60. For example, stop 38 may be moveable such that when sheath 50 is advanced to be positioned over groove 60 of hook feature 36, stop 38 may be repositioned to keep sheath 50 from pushing back to the previous position. Alternatively, handle 54 of sheath 50 may include a lock feature, such as a tab, that can be pushed down to fill the space between stop 38 and handle 54 when sheath 50 was pushed forward to cover the opening of groove 60. In a further example, handle 54 itself may be designed to interact with handle 32 of rod 30 to position sheath 50 in different positions, as described in further detail with respect to FIGS. 11-13. As another example, the implant tool may include a separate stop feature that is added between handle 54 of sheath 50 and the stop feature 38 of rod 30 when sheath 50 is advanced to cover the opening of groove 60. In any case, the element, whether it be a moveable stop, a portion of handle 54 of sheath 50 or a separate stop may be removed when sheath 50 is to no longer cover the opening of groove 60 of hook feature 36.

Although FIG. 7 is illustrated and described in the context of hook feature 36, rod 30 may include other attachment features. For example, rod 30 may include the attachment feature described in FIGS. 13A and 13B or other attachment feature. Sheath 50 may be positioned to interact with the lead 16 or the attachment feature of rod 30 to more securely attach lead 16 to the implant tool.

Figure 8A:
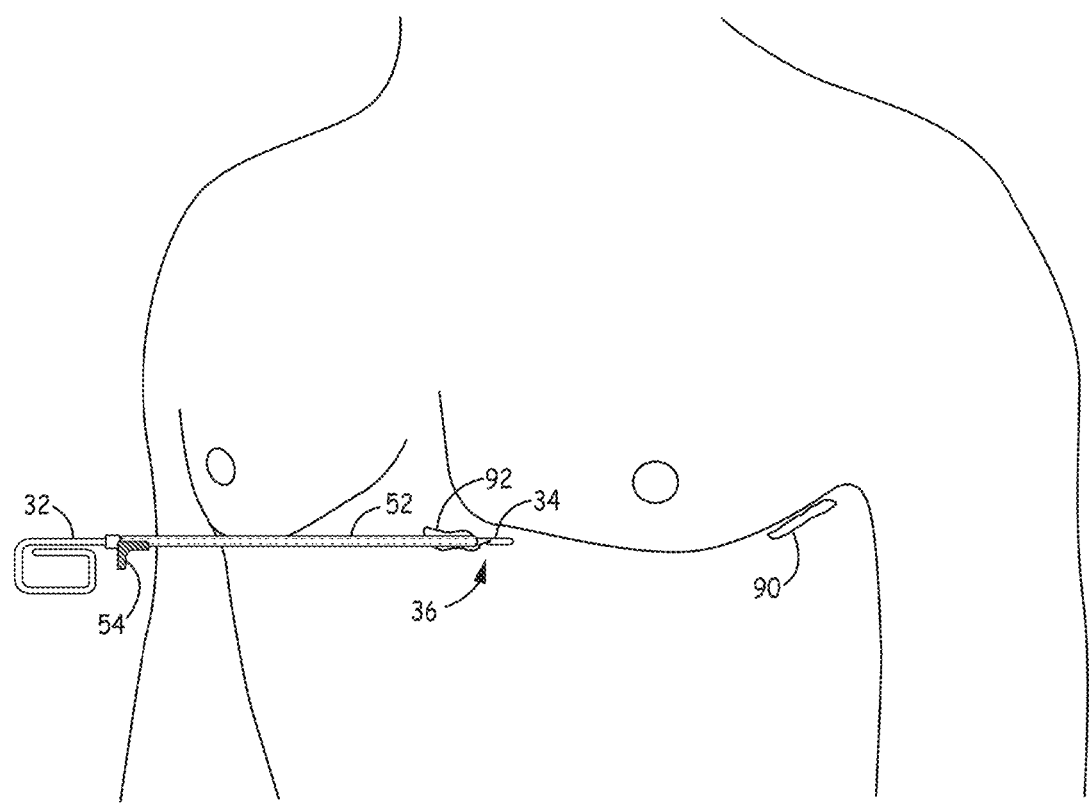
FIGS. 8A-I illustrate an example method of implanting an implantable medical lead using an implant tool in accordance with this disclosure.

FIGS. 8A-I illustrate an example method of implanting an implantable medical lead, such as defibrillation lead 16, using an implant tool, such as the implant tool illustrated in FIGS. 2A and 2B. The techniques illustrated in FIG. 8, however, may be performed using other implant tools described herein. As illustrated in FIG. 8A, a first incision 90 is made at a location on the side of the torso of patient 12 and a second incision 92 is made at a location near the center of the torso of patient 12. For example, first incision 90 may be made between the anterior axillary line and the posterior axillary line on the left side of patient 12 and second incision 92 may be made near the xiphoid process of patient 12. However, first incision 90 and second incision 92 may be made at other locations on the side and center of the torso, respectively. For example, second incision 92 may be offset to the left or right of the xiphoid process of patient 12. As another example, second incision 92 may be made superior or inferior to the xiphoid process of the patient. Although described herein as first and second incisions, the incisions may be made in any order.

Figure 8B:
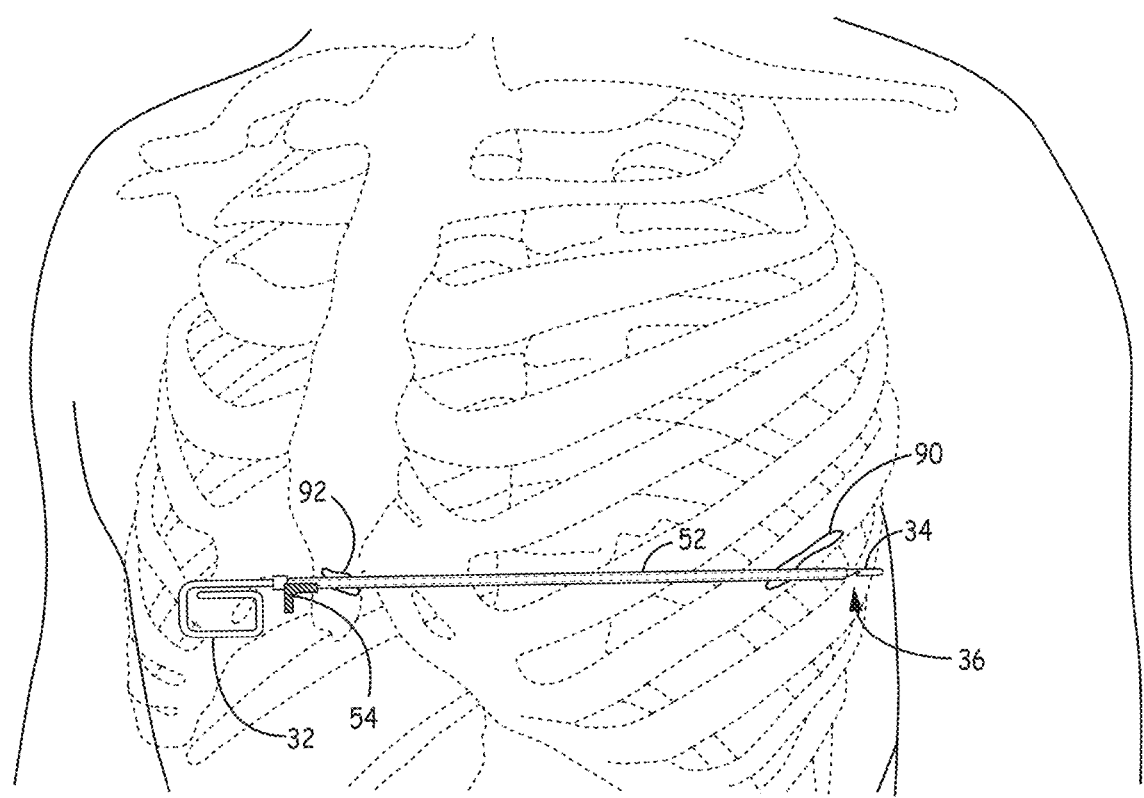

Sheath 50 is placed over rod 30 (e.g., as show in FIG. 2B). The distal end of rod 30 is introduced into second incision 92 (as shown in FIG. 8A) near the center of patient 12. The implant tool is advanced through the subcutaneous tissue from second incision 92 to first incision 90 (as shown in FIG. 8B). The implant tool may be advanced until the distal end of rod 30 and the distal end of sheath 50 exit through first incision 90 or are close enough to first incision 90 such that the user may access hook feature 36 (or other attachment feature) of rod 30. As described above with respect to FIG.

2, the distal end of rod 30 may be shaped to aid in tunneling through subcutaneous tissue from second incision 92 to first incision 90. For example, the distal end of rod 30 may be blunt, rounded, or otherwise shaped to enable a user to tunnel through subcutaneous tissue without damaging surrounding tissue or puncturing through the skin of patient 12.

Figure 8C:
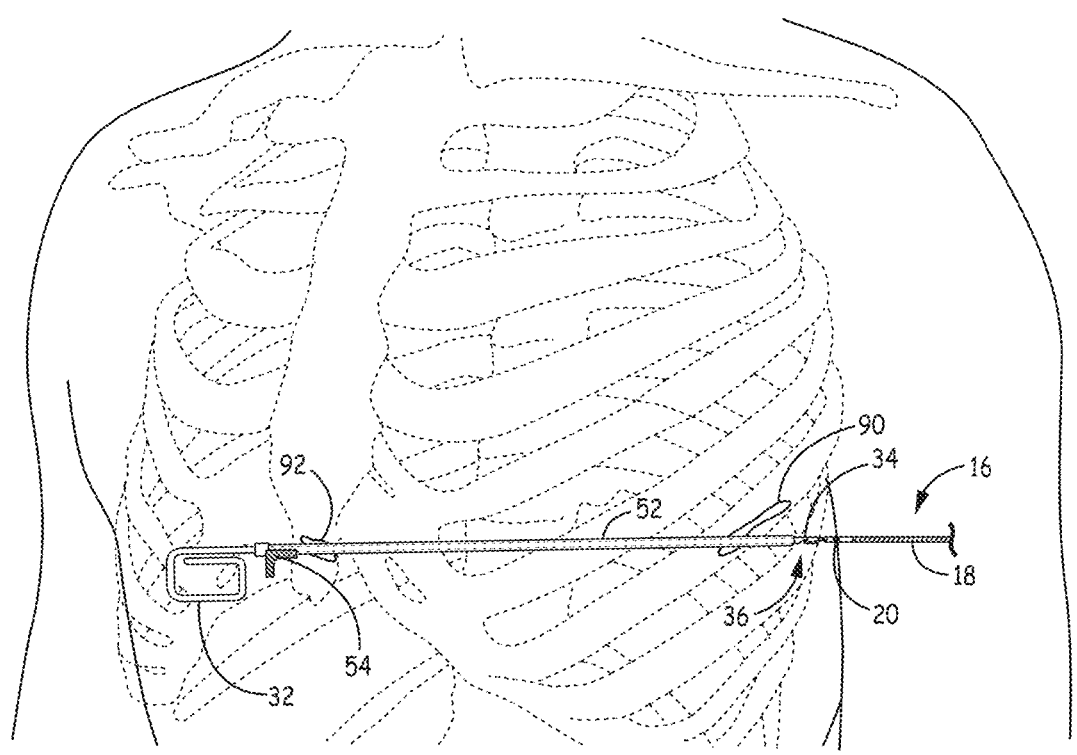

The distal end of defibrillation lead 16 is attached to hook feature 36 (or other attachment feature) of rod 30 (as illustrated in FIG. 8C). For example, attachment feature 29 may be placed in groove 60 of hook feature 36 of rod 30 and sheath 50 may be advanced toward the distal end of rod 30 until sheath 50 covers the opening of hook feature 36 (as illustrated and described in detail with respect to FIGS. 7A and 7B).

Figure 8D:
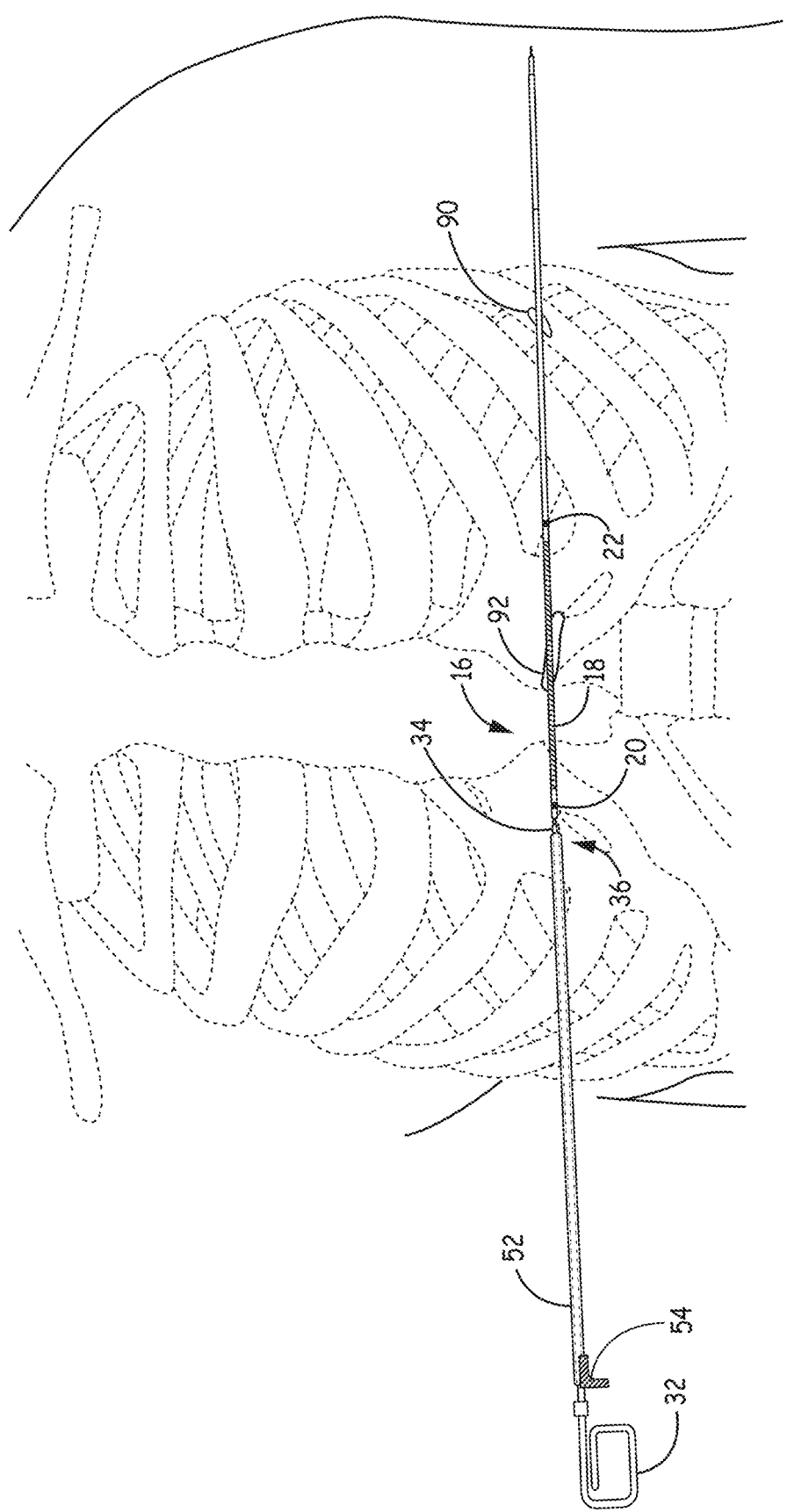

Rod 30 is pulled toward second incision 92 thereby pulling lead 16 through the subcutaneous path formed from the second incision 92 to the first incision 90 during the previous tunneling of rod 30 until rod 30 and the distal end of lead 16 exit second incision 92 (as illustrated in FIG. 8D). Sheath 50 remains in place on shaft 34 of rod 30 during the pulling of the distal end of rod 30 from first incision 90 to second incision 92. As described above, sheath 50 may be sized to form an interference fit on shaft 34 of rod 30 to keep sheath 50 in place on rod 34. Alternatively or additionally, the user may place a finger over handle 54 of sheath 50 to keep sheath 50 in place on rod 34 or handle 54 of sheath 50 may be locked into a position to hold sheath 50 in place on rod 34. Defibrillation lead 16 now partially resides within the subcutaneous tissue from first incision 90 to second incision 92 with the distal end of lead 16 extending out of second incision 92, the proximal end of lead 16 extending out of first incision 90, and the remainder of lead 16 is subcutaneously located in the tunnel formed by rod 30.

The steps illustrated in FIG. 8A-8C are for illustrative purposes only and should not be considered limiting of the techniques described herein. The user may place defibrillation lead 16 along the path from first incision 90 to second incision 92 in other manners. For example, rod 30 and sheath 50 may be advanced through the subcutaneous tissue from first incision 90 to second incision 92. In this case, an attachment feature of the proximal end of lead 16 may be placed within an attachment feature of rod 30 (such as the attachment features described in FIGS. 13A and 13B and the lead may be pulled from incision 92 to incision 90 thereby placing a portion of lead 16 in the subcutaneous path formed during the previous tunneling of rod 30.

Figure 8E:
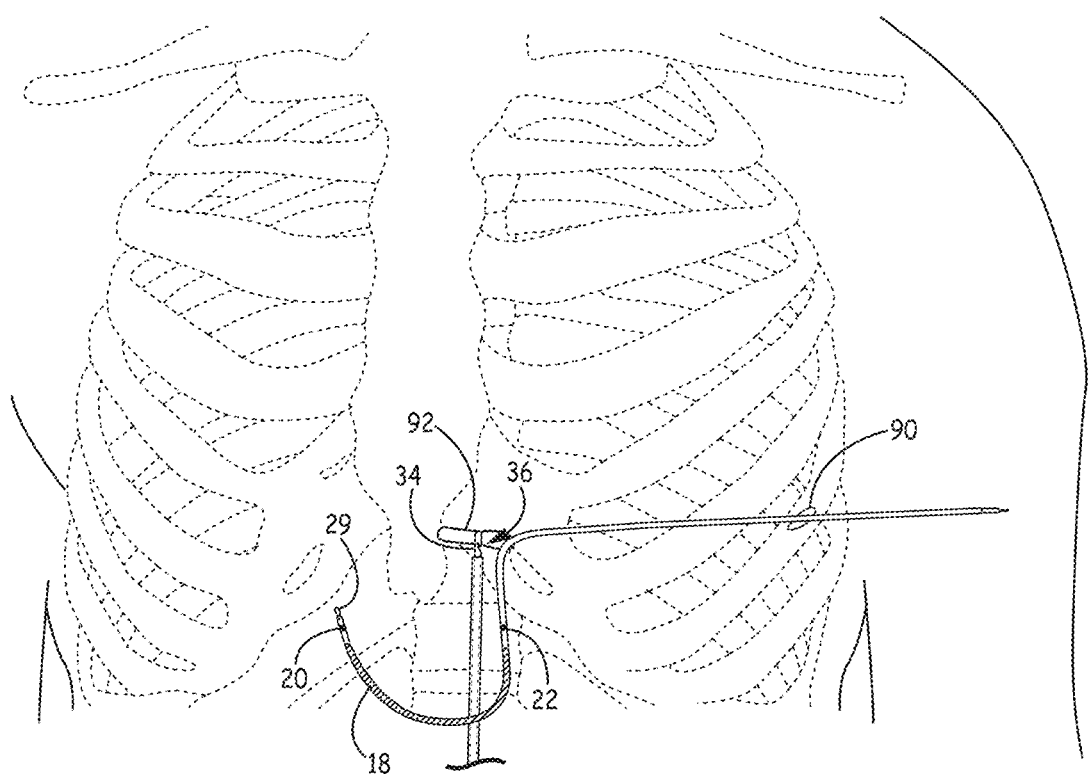
Figure 8F:
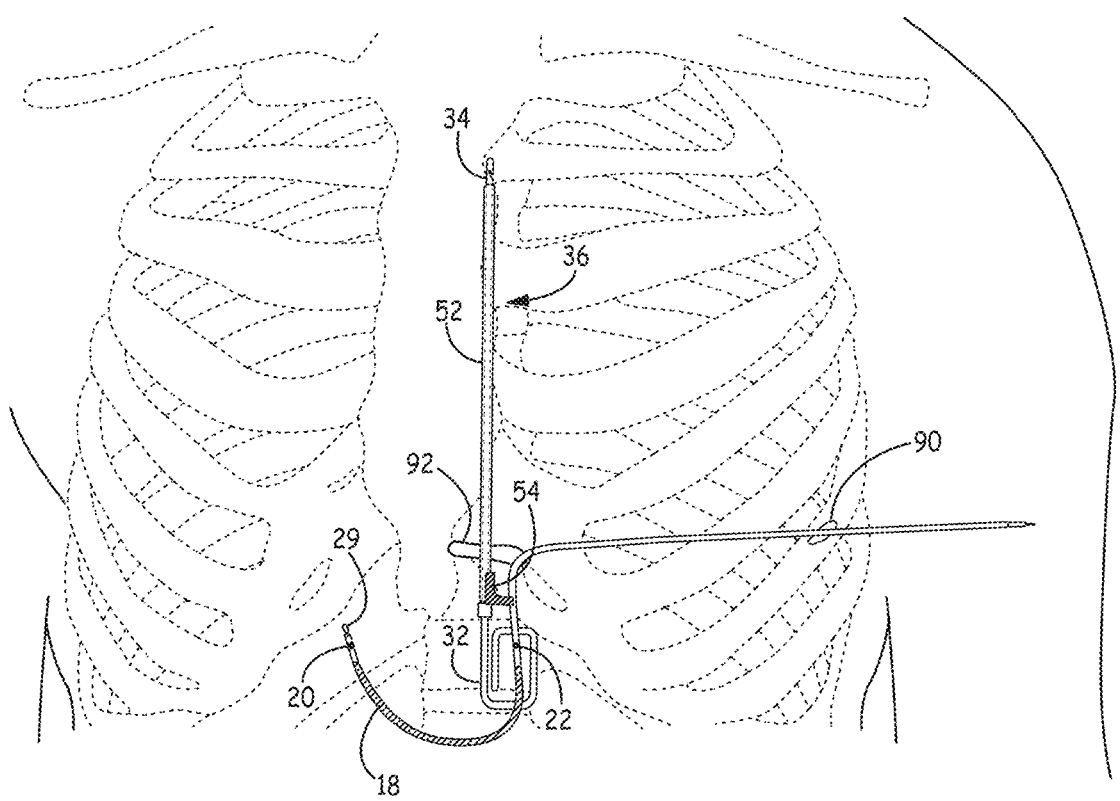

The distal end of rod 30 and sheath 50 are then introduced into second incision 92 near the center of the torso of patient 12 (as illustrated in FIG. 8E). Rod 30 is advanced subcutaneously superior from second incision 92 substantially parallel to sternum 28 (as illustrated in FIG. 8F). In the example illustrated in FIG. 8F, the path followed by rod 30 is offset laterally to the left of the body of sternum 28 and the distal end of rod 30 is positioned near the second rib of patient 12. Such a path enables defibrillation lead 16 to be implanted such that the defibrillation energy delivered via electrode 18 returns to the housing electrode of ICD 14 through the left ventricle of heart 26. However, rod 30 may be advanced along other paths. For example, the path followed by rod 30 may be offset from sternum 28 on the right side of sternum 28, over sternum 28 or other path depending on the anatomy of patient 12 and/or location of ICD 14. As another example, distal end of rod 30 may be positioned further superior or inferior depending on the location of ICD 14 relative to lead 16, placement of electrodes 18, 20 and 22 on lead 16, and other factors.

In instances in which sheath 50 and/or rod 30 include markings, the user may determine the location of the distal end of rod 30 based on the markings. In this manner, the user may utilize the markings on rod 30 or sheath 50 to aid in determining the location of the tunnel, e.g., how far rod 30 has advanced within patient 12. The markings may also be used to determine orientation of a distal feature (e.g., a bend or curve). This may be particularly useful in instances in which the patient is obese or the rod is tunneled underneath/below the sternum as the location of rod 30 may be more difficult to visualize.

Figure 8G:
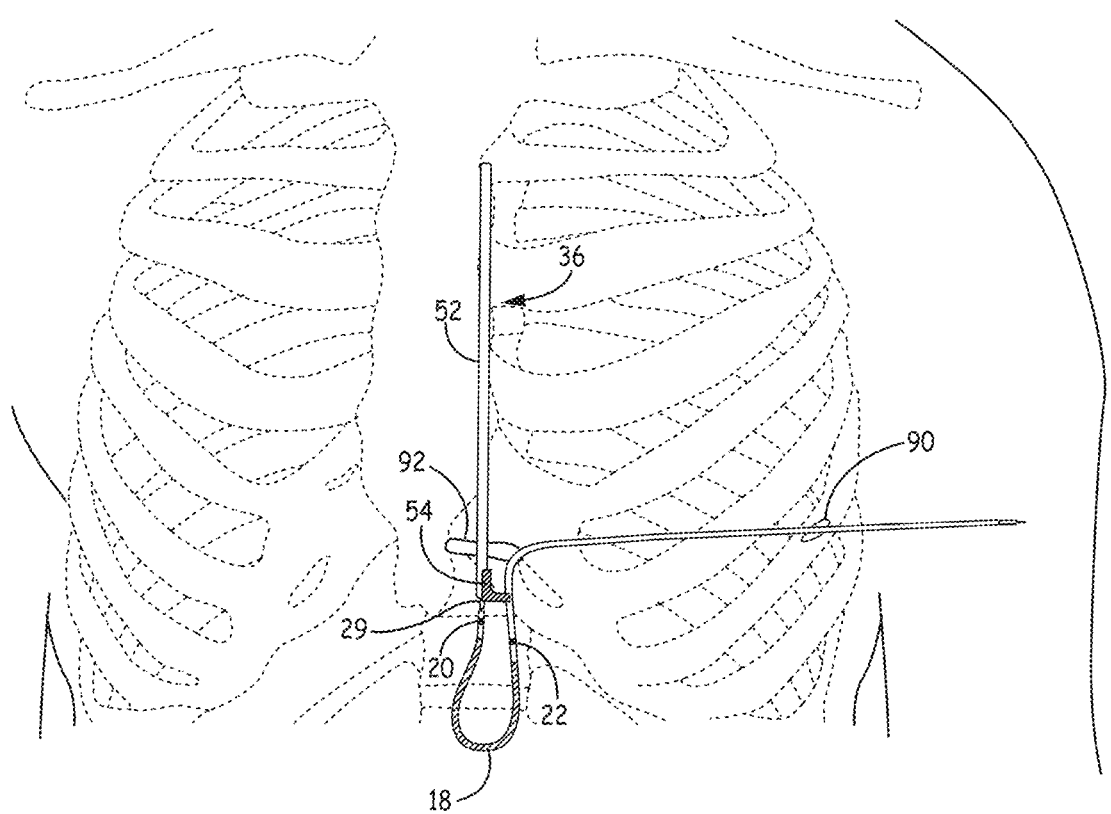
Figure 8H:
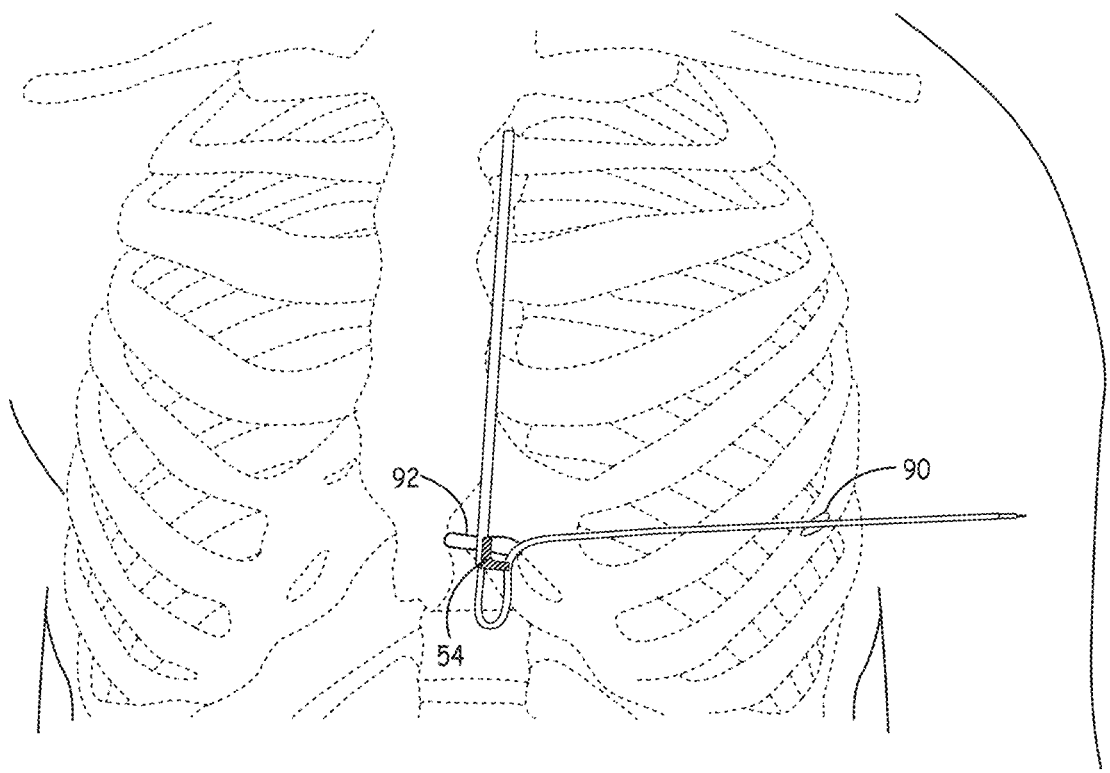

While sheath 50 is held in place, rod 30 is pulled toward second incision 92 until rod 30 exits the body of patient 12 thus leaving sheath 50 in place along the path within the body of patient 12 (as illustrated in FIG. 8G). The distal end of lead 16 is introduced into the inner channel of sheath 50 and advanced along the inner channel of sheath 50 from second incision 92 toward the distal end of sheath 50 (as illustrated in FIG. 8H).

Figure 8I:
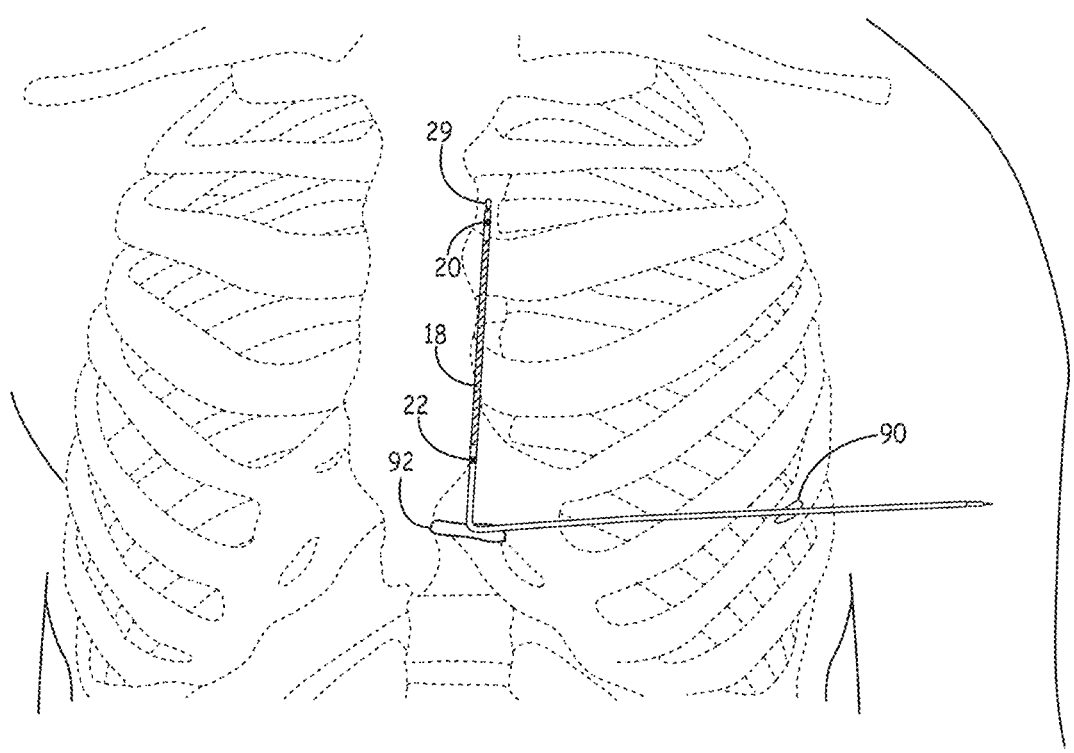

Lead 16 is removed from the inner channel of sheath 50 and sheath 50 is removed from the body of patient 12 while leaving defibrillation lead 16 in place (as illustrated in FIG. 8I). Sheath 50 may be peeled off lead 16 via opening 62 as described with respect to sheath 60 of FIG. 3, split and peeled off along a score line 83 or other weak portion of the sheath as described with respect to sheath 80 of FIG. 5, or slit using a slitter and peeled off as described with respect to sheath 86 of FIG. 6. In some instances, the distal end of lead 16 may include an anchoring mechanism to fixate the distal end of lead 16 in place near the superior location (e.g., near the second or third rib). The anchoring mechanism may include tines, a helix, or other anchoring mechanisms. In other examples, a third incision may be made toward the top of sternum 28 proximate the desired location of the distal end of defibrillation lead 16. In this case, rod 30 may be advanced subcutaneously from second incision 92 to the third incision until distal end 38 exits through the third incision. The distal end of defibrillation lead 16 would also be advanced through sheath 50 until it is adjacent to the third incision. The distal end of defibrillation lead 16 may then be affixed to the desired location proximate the third incision via a fixation mechanism separate from defibrillation lead 16, e.g., sutures, staples, anchor sleeve, or the like, or built into defibrillation lead 16, e.g., tines, helix or other built in fixation mechanism.

The portion of defibrillation lead 16 proximate second incision 92 may also be affixed to the desired location proximate second incision 92 via a fixation mechanism separate from defibrillation lead 16, e.g., sutures, staples, anchor sleeve, or the like, or built into defibrillation lead 16, e.g., tines, helix or other built in fixation mechanism.

A subcutaneous pocket may be created near first incision 90 and ICD 14 may be placed within the subcutaneous pocket. A connector of defibrillation lead 16 is mechanically coupled to the connector block of ICD 14. The various incision and pockets may then be closed to complete the implant procedure.

The example method of implanting a lead illustrated in FIGS. 8A-I are exemplary in nature and should not be considered limiting of the techniques described in this disclosure. The lead may be inserted using the implant tool of FIGS. 2A and 2B any of a number of ways, which is one of the advantages of such a tool. The implant tool may be used by the user to pull lead 16 through the subcutaneous tissue (as described above with respect to FIGS. 8A-D) between any two incisions in any direction or used by the user to push lead 16 through the subcutaneous tissue by creating the path, placing the sheath and pushing either the proximal or distal end of the lead through the sheath (similar to the steps described above with respect to FIGS. 8E-I). In the example in which a third incision is made superior to the second incision, lead 16 may be pulled from either the second incision to the third incision via an attachment feature (e.g., 29) at the distal end of lead 16 or from the third incision to the second incision via an attachment feature (e.g., terminal pin of the connector) at the proximal end of lead 16. In some instances, sheath 50 may be sized to have an interference fit with the connector on the proximal end of lead 16 or by having an attachment feature on rod 30 configured to attach or couple to the connector or other portion of the proximal end of lead 16. As such, the implant tool having rod 30 and sheath 50 thus provides the user flexibility to perform lead insertion via either a pull method, a push method or a combination push and pull method.

In other examples, rod 30 may be introduced into second incision 92 and advanced to create a tunnel or path that is not subcutaneous, but instead is substernal. For example, rod 30 may be advanced under/below the sternum. Description of other locations are provided above with respect to FIG. 1.

As described above with respect to FIG. 3, rod 30 and/or sheath 50 may include markings 65 that coincide with features on lead 16, such as markings 65 that coincide with electrodes 18, 20 and 22 when the distal end of lead 16 is located at the distal end of sheath 50. In such cases, prior to tunneling or prior to creating incisions 90 and 92, the user may place the implant tool on the skin of the patient such that the markings of rod 30 and/or sheath 50 coincide with a desired location of the electrodes 18, 20 and 22 of lead 16 and place landmarks on the skin of patient 12 corresponding with a desired end point of a tunnel or a desired tunneling path that places the features (e.g., electrodes 18, 20, and 22) of lead 16 at the desired location.

Figure 9A:
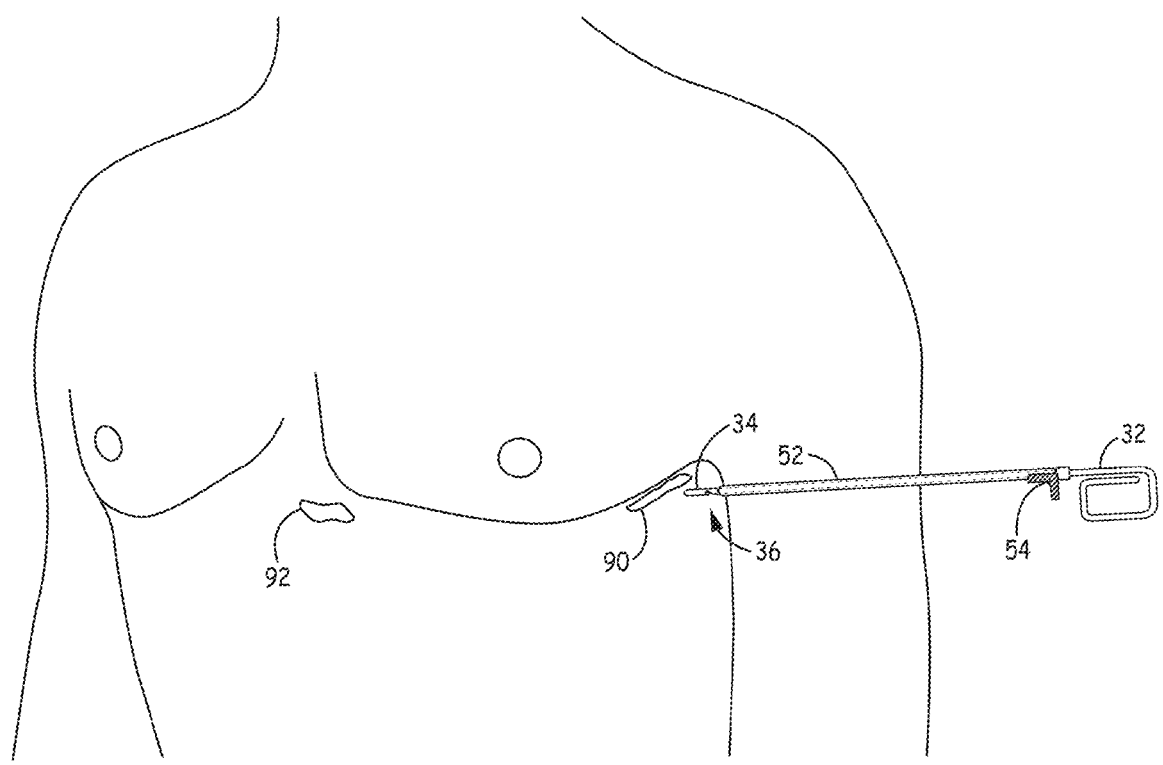
FIGS. 9A-9I illustrated another example method of implanting an implantable medical lead using an implant tool in accordance with this disclosure.

FIGS. 9A-9I illustrated another example method of implanting an implantable medical lead, such as defibrillation lead 16, using an implant tool, such as the implant tool illustrated in FIGS. 2A and 2B. The techniques illustrated in FIG. 9, however, may be performed using other implant tools/kits described herein. As illustrated in FIG. 9A, a first incision 90 is made at a location on the side of the torso of patient 12 and a second incision 92 is made at a location near the center of the torso of patient 12. For example, first incision 90 may be made between the anterior axillary line and the posterior axillary line on the left side of patient 12 and second incision 92 may be made near the xiphoid process of patient 12. However, first incision 90 and second incision 92 may be made at other locations on the side and center of the torso, respectively. For example, second incision 92 may be offset to the left or right of the xiphoid process of the patient. As another example, second incision 92 may be made superior or inferior to the xiphoid process of the patient. Although described herein as first and second incisions, the incisions may be made in any order.

Figure 9B:
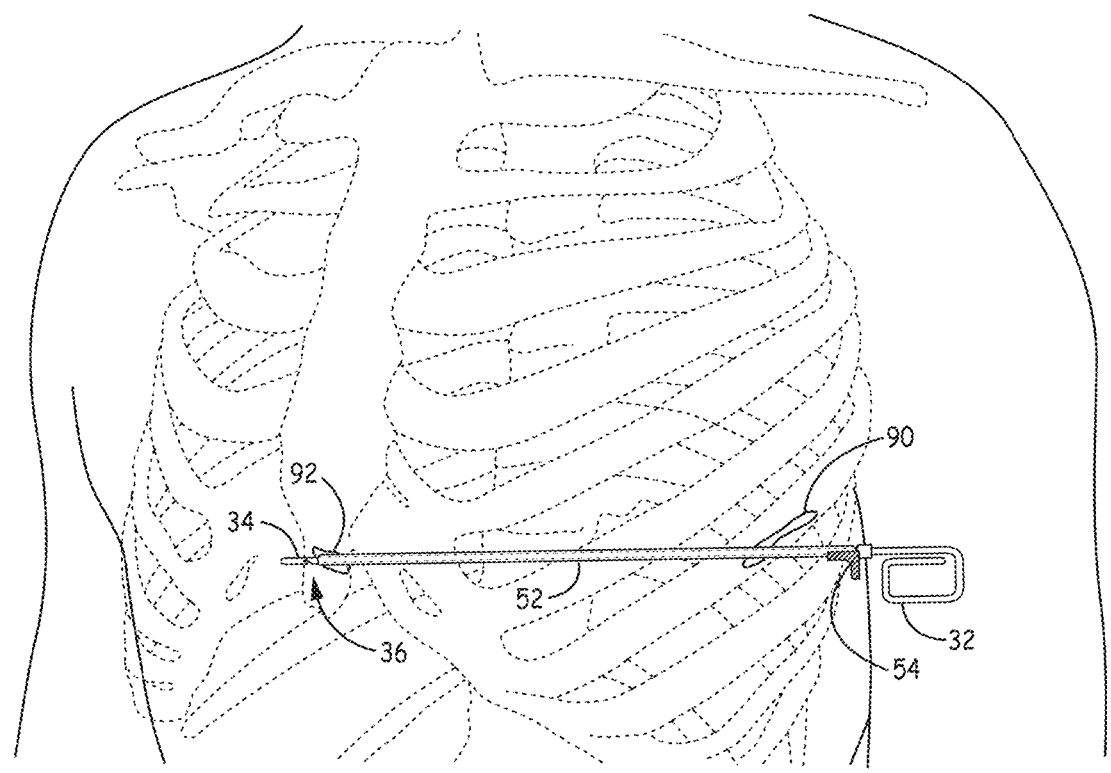

Sheath 50 is placed over rod 30 (e.g., as show in FIG. 2B). The distal end of rod 30 is introduced into first incision 90 (as shown in FIG. 9A) on the left side of patient 12. Rod 30 and sheath 50 are advanced through the subcutaneous tissue from first incision 90 to second incision 92 (as shown in FIG. 9B). The implant tool may be advanced until the distal end of rod 30 and the distal end of sheath 50 exit through first incision 90 or are close enough to first incision 90 such that the user may access sheath 50. As described above with respect to FIG. 2, the distal end of rod 30 may be shaped to aid in tunneling through subcutaneous tissue from first incision 90 to second incision 92. For example, the distal end of rod may be blunt, rounded, or otherwise shaped to enable a user to tunnel through subcutaneous tissue without damaging surrounding tissue or puncturing through the skin of patient 12.

Figure 9C:
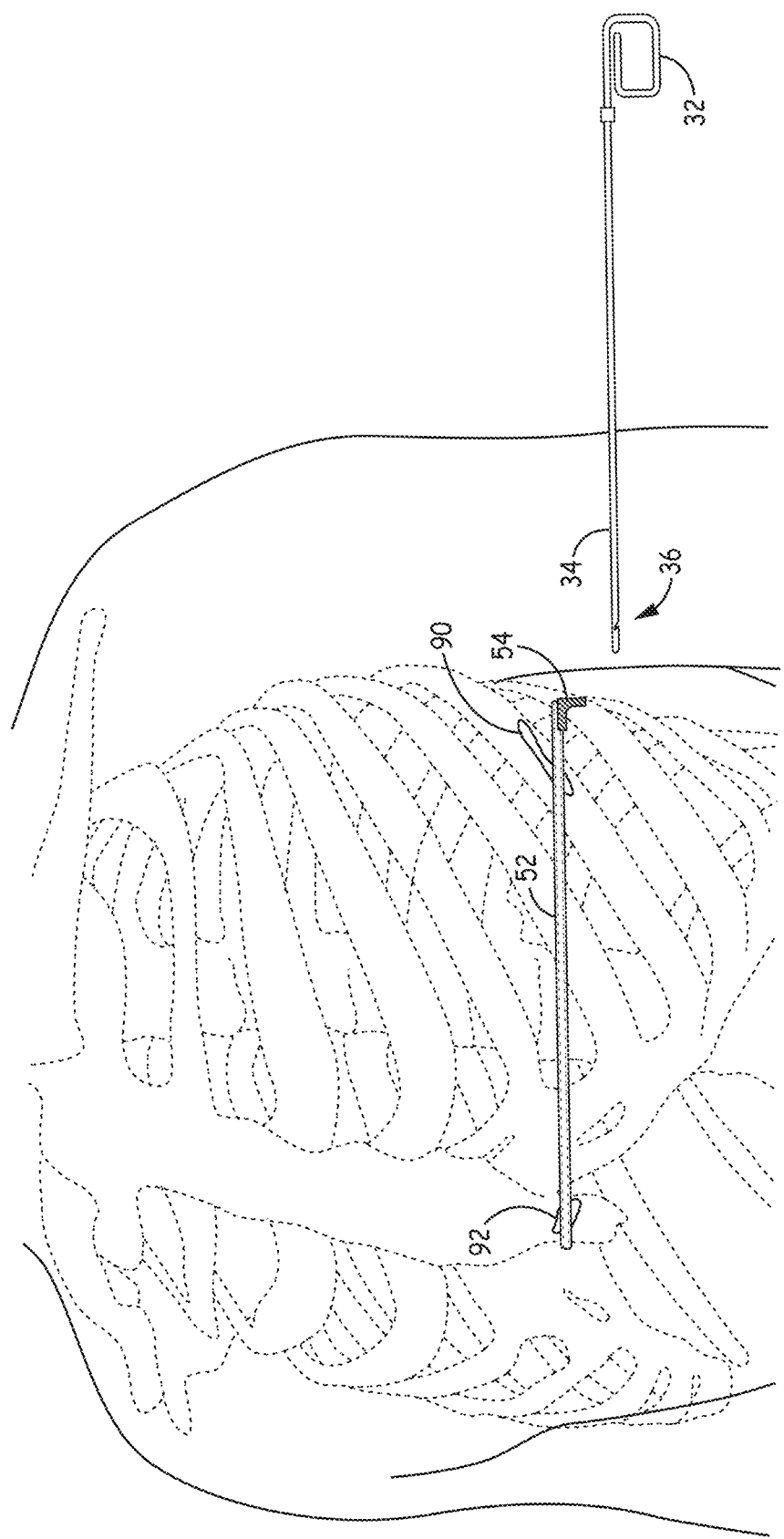
Figure 9D:
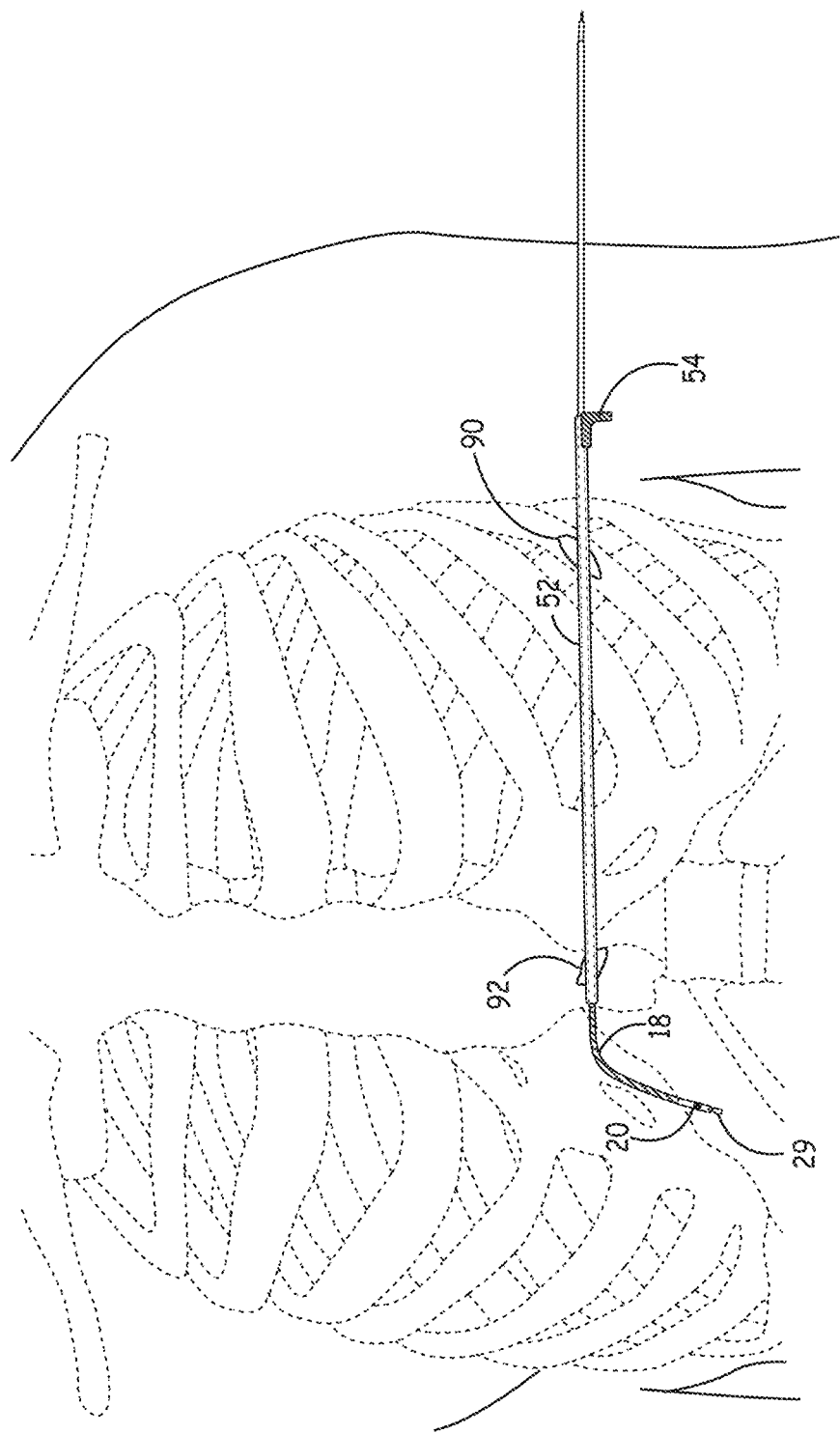

While sheath 50 is held in place, rod 30 is pulled toward first incision 90 until rod 30 exits the body of patient 12 thus leaving sheath 50 in place within the body of patient 12 from the first incision 90 to the second incision 92 (as illustrated in FIG. 9C). The distal end of lead 16 is introduced into the inner channel of sheath 50 near first incision 90 and advanced along the inner channel of sheath 50 from first incision 90 until the distal end of lead 16 exits out the distal end of sheath 50 and second incision 92 (as illustrated in FIG. 9D). In other instances, the proximal end of lead 16 may be introduced into channel 58 near incision 92 and advanced toward incision 90. Alternatively rod 30 and sheath 50 may be advanced from second incision 92 to first incision 90, rod 30 may be removed leaving sheath 50 in place and lead 16 may be advanced either from incision 90 to incision 92 or from incision 92 to incision 90.

Figure 9E:
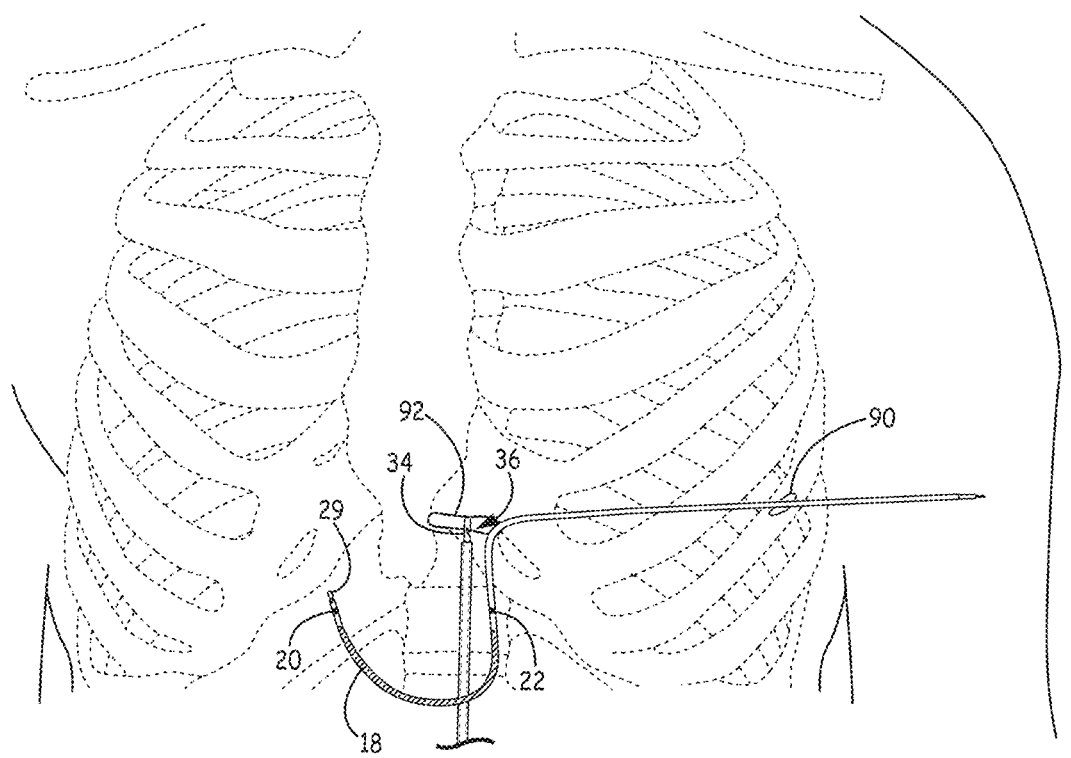

Lead 16 is removed from the inner channel of sheath 50 and sheath 50 is removed from the body of patient 12 while leaving defibrillation lead 16 in place (as illustrated in FIG. 9E). Sheath 50 may be peeled off lead 16 via opening 62 as described with respect to sheath 60 of FIG. 3, split and peeled off along a score line 83 or other weak portion of the sheath as described with respect to sheath 80 of FIG. 5, or slit using a slitter and peeled off as described with respect to sheath 86 of FIG. 6. Defibrillation lead 16 now partially resides within the subcutaneous tissue from first incision 90 to second incision 92 with the distal end of lead 16 extending out of first incision 90, the proximal end of lead 16 extending out of second incision 92, and the remainder of lead 16 is subcutaneously located in the tunnel formed by rod 30.

Figure 9F:
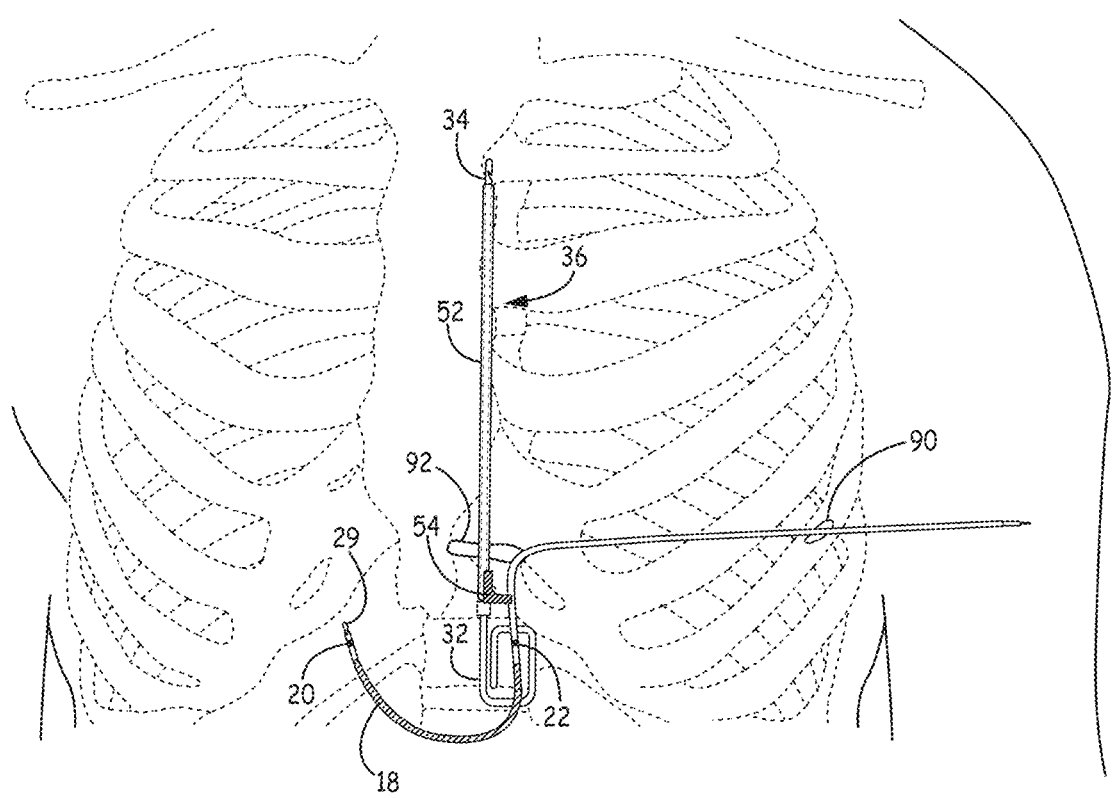

The same or a new sheath 50 is then replaced on shaft 34 of rod 30. The distal end of rod 30 and sheath 50 are then introduced into second incision 92 near the center of the torso of patient 12 (as illustrated in FIG. 9E). Rod 30 is advanced subcutaneously superior from second incision 92 (as illustrated in FIG. 9F). In instances in which sheath 50 and/or rod 30 include markings, the user may determine the location of the distal end of rod 30 based on the markings.

Figure 9G:
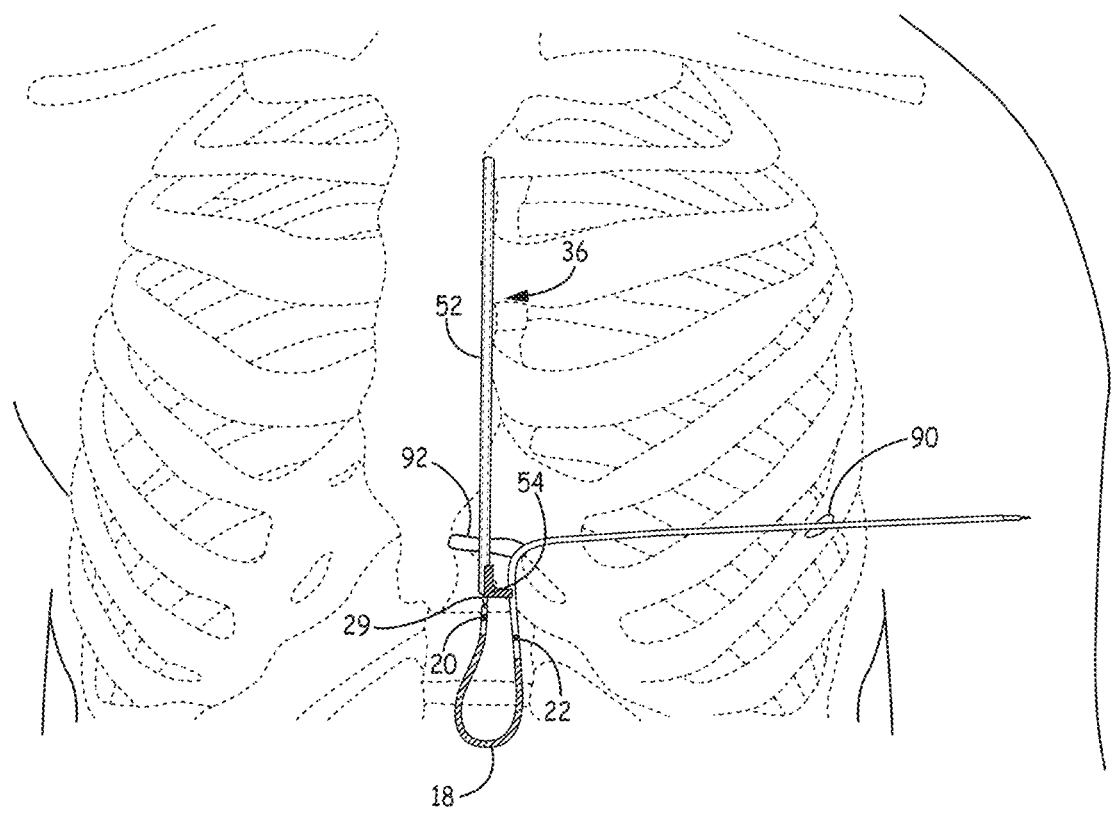
Figure 9H:
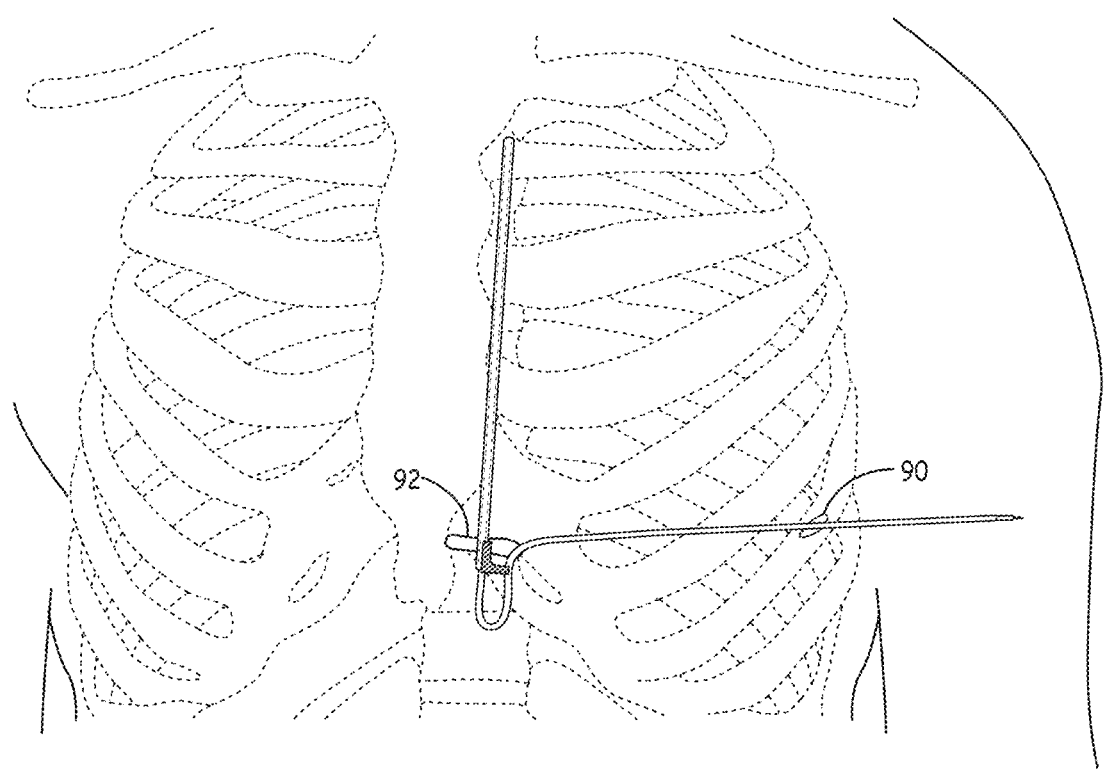
Figure 9I:
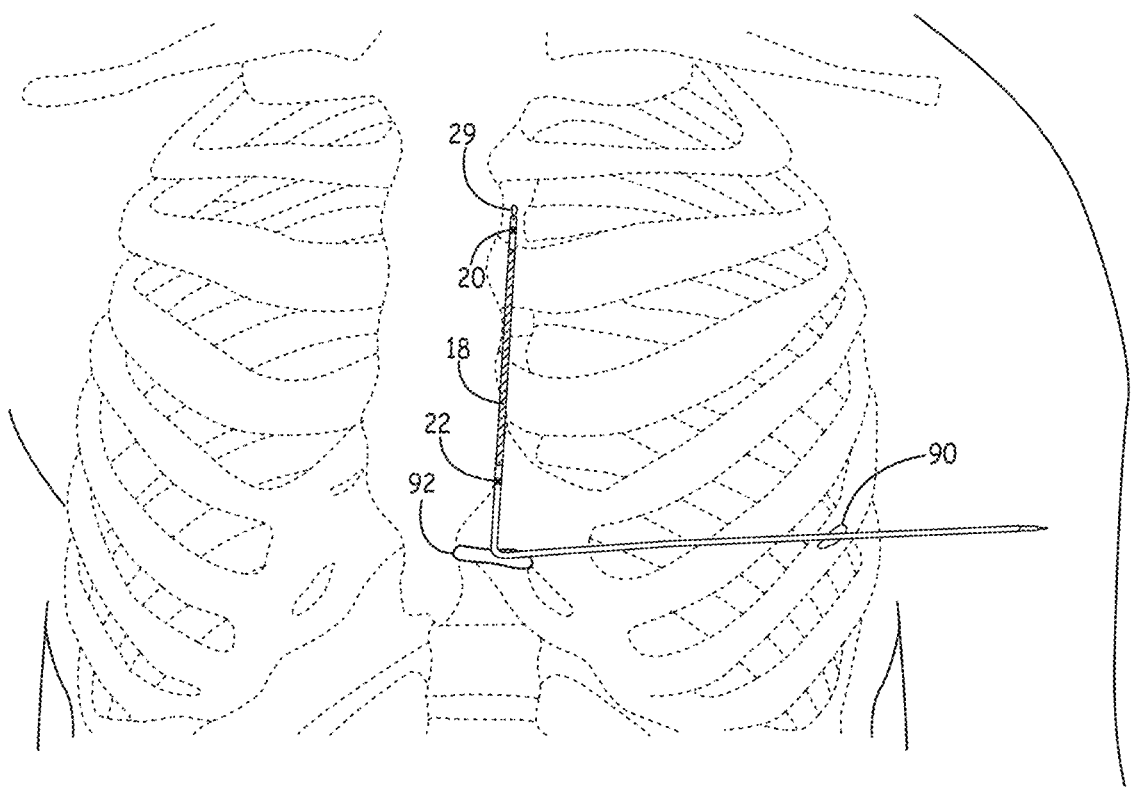

While sheath 50 is held in place, rod 30 is pulled toward second incision 92 until rod 30 exits the body of patient 12 thus leaving sheath 50 in place within the body of patient 12 (as illustrated in FIG. 9G). The distal end of lead 16 is introduced into the inner channel of sheath 50 near second incision 92 and advanced along the inner channel of sheath 50 from second incision 92 toward the distal end of sheath 50 (as illustrated in FIG. 9H). When at the desired location, lead 16 is removed from the inner channel of sheath 50 and sheath 50 is removed from the body of patient 12 (as illustrated in FIG. 9I). Sheath 50 may be peeled off lead 16 via opening 62 as described with respect to sheath 60 of FIG. 3, split and peeled off along a score line 83 or other weak portion of the sheath as described with respect to sheath 80 of FIG. 5, or slit using a slitter and peeled off as described with respect to sheath 86 of FIG. 6.

The example method of implanting a lead illustrated in FIGS. 9A-9I is exemplary in nature and should not be considered limiting of the techniques described in this disclosure. In other examples, rod 30 may be introduced into second incision 92 and advanced to create a tunnel or path that is not subcutaneous, but instead is substernal. For example, rod 30 and sheath 50 may be advanced under/below the sternum. Description of other locations are provided above with respect to FIG. 1.

As described above with respect to FIG. 3, rod 30 and/or sheath 50 may include marking that coincide with features on lead 16, such as markings that coincide with electrodes 18, 20 and 22 when the distal end of lead 16 is located at the distal end of sheath 50. In such cases, prior to tunneling or prior to creating incisions 90 and 92, the user may place the implant tool on the skin of the patient such that the markings of rod 30 and/or sheath 50 coincide with a desired location of the electrodes 18, 20 and 22 of lead 16 and place landmarks on the skin of patient 12 corresponding with a desired end point of a tunnel or a desired tunneling path that places the features (e.g., electrodes 18, 20, and 22) of lead 16 at the desired location.

As illustrated in FIGS. 8 and 9, implant tools in accordance with the techniques of this disclosure permit implantation of an implantable medical lead any of a number of ways, which is one of the advantages of such a tool. Although illustrated as being performed with the implant tool of FIGS. 2A and 2B, the techniques described above in FIGS. 8 and/or 9 may be performed using any of the various tools described herein.

Figure 11:
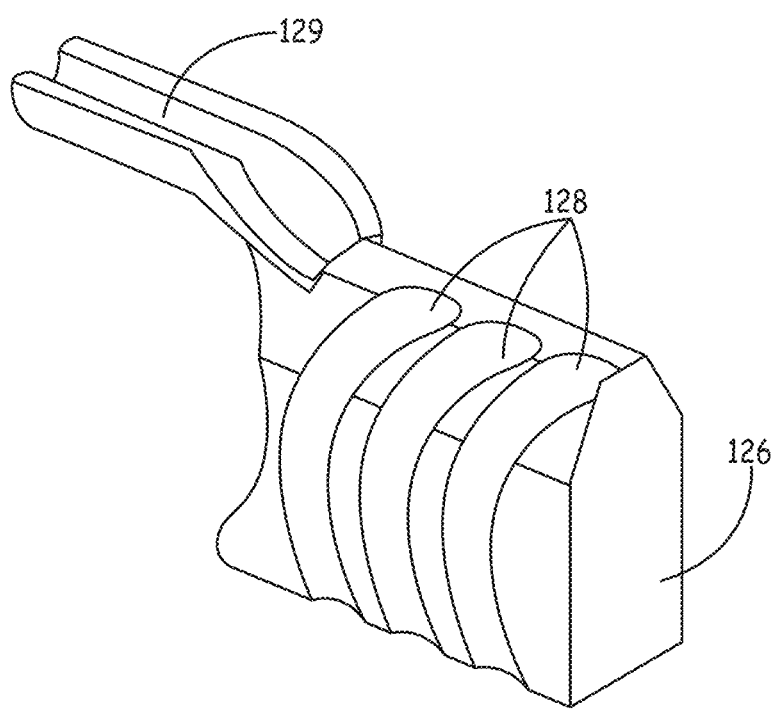
FIG. 11 illustrates an enlarged view of the handle of the sheath of FIG. 10.

FIG. 11 illustrates an example of another implant tool that includes a rod 120 and a sheath 122. Repetitive description of like numbered elements in other embodiments is omitted for sake of brevity. Rod 120 can include one or more of the structure and/or functionality of rod 30 (and vice versa). Rod 120 is substantially similar to rod 30 of FIG. 2A except that rod 120 has a different shaped handle 32' and no stop 38.

Sheath 122 can include one or more of the structure and/or functionality of sheath 50, 60, 80 and/or 86 (and vice versa) and may be used with any of the rods described herein. Sheath 122 is substantially similar to sheath 50 of FIGS. 2 and 3 except that sheath 122 has a different handle 126. Handle 126 of sheath 122 includes a plurality of grooves 128 spaced apart from one another. The distance between each of grooves 128 may be equal or different. FIG. 11 illustrates an enlarged view of handle 126 of sheath 122. The example handle 126 of sheath 122 includes three grooves 128, but handle 126 may include more or fewer grooves 128. In some instances, handle 126 may include only a single groove. Grooves 128 are shaped to conform to the curved portion of the proximal end of handle 32' of rod 120. Handle 126 also includes a groove 129 that receives the proximal portion of sheath 122.

FIGS. 12A and 12B illustrate sheath 122 placed in two positions on rod 120. FIG. 12A illustrates a first position in which the curved portion of the distal end of handle 32' of rod 120 is positioned within the most distal groove 128 of handle 126. In this position, sheath 122 extends along the majority of the length of shaft 34, but does not cover the opening of hook feature 36.

When attachment feature 29 of lead 16 is placed within the groove of hook feature 36, sheath 122 may be moved from the first position to a second position illustrated in FIG. 12B. In the second position, the curved portion of the distal end of handle 32' of rod 120 is positioned within the subsequent groove 128 toward a proximal end of handle 126 (the middle groove in FIG. 12). To place sheath 122 in the second position, the user may rotate sheath 122, push sheath 122 forward slightly, and rotate sheath 122 back to its original orientation to place handle 32' within the second groove 128. In the second position, body 52 of sheath 122 covers the opening of hook feature 36 such that attachment feature 29 of lead 16 does not exit hook feature 36 while being pulled through a tunnel within body of patient 12.

In a further example, sheath 122 may be placed in a third position (not illustrated in FIGS. 12A and 12B) in which the curved portion of the distal end of handle 32' of rod 120 is positioned within the most distal groove 128 of handle 126. In the third position, sheath 122 may extend beyond the distal end of rod 120 and cover a portion of lead 16 (e.g., a distal end of lead 16 or a connector of lead 16), which may aid in pulling lead 16 through the subcutaneous tunnel. Alternatively, a distal end of sheath 50 may be sized to provide an interference fit with a connector or other portion of lead 16.

Figure 13A:
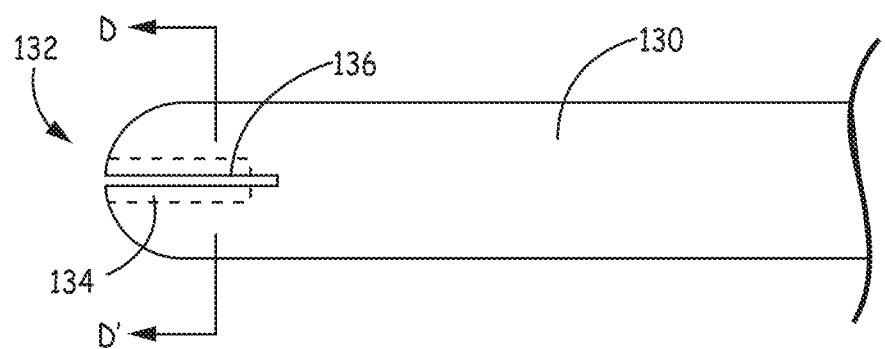
FIGS. 13A and 13B illustrates a distal end of an alternative attachment feature of a rod.
Figure 13B:
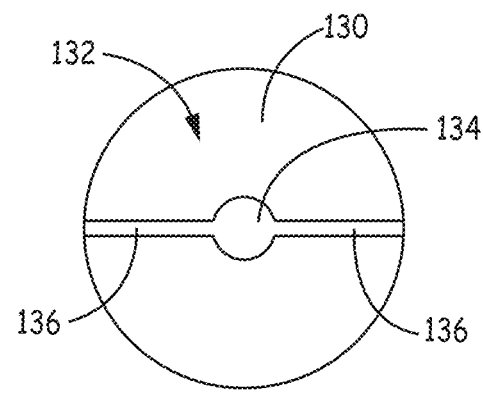

FIGS. 13A and 13B illustrates a distal end of an alternative attachment feature of a rod 130. Rod 130 can include one or more of the structure and/or functionality of rod 30 and/or 120 (and vice versa). Rod 130 is substantially similar to rod 30 and 120 except that rod 130 includes an attachment feature 132 at the distal end of rod 130. FIG. 13A illustrates a side view of the distal end of rod 130 and FIG. 13B illustrates a cross-sectional view of the distal end of rod 130 taken from D-D'.

Attachment feature 132 of rod 130 includes a round recess 134 that extends into a center of the distal end of rod 130 and a slit 136 that extends across the diameter and into the distal end of rod 130. The recess may extend within a non-centered portion of rod 130 (e.g., offset to a side). In the example illustrated in FIG. 13A, slit 136 extends further proximal along the length of the rod than recess 134, but that need not be the case. Round recess 134 is sized to interact with a terminal pin of a connector on the proximal end of lead 16. For example, the diameter of recess 134 may be sized to be equal to or slightly smaller than the diameter of the terminal pin of a connector. In this manner, the user of the implant tool may push the terminal pin of the connector of lead 16 into recess 134, slightly expanding slit 136, which creates an interference fit with the terminal pin to couple lead 16 to rod 130.

Figure 14:
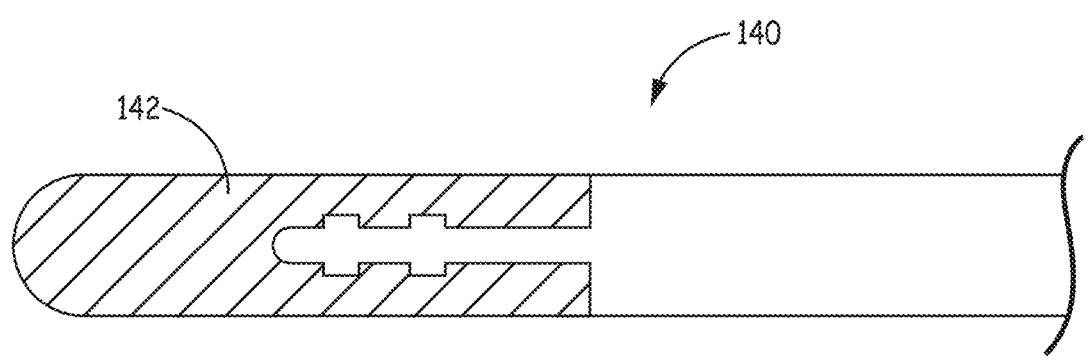
FIG. 14 illustrates a distal portion of another example rod.

FIG. 14 illustrates a distal portion of an alternative rod 140. Rod 140 can include one or more of the structure and/or functionality of rods 30, 120, and/or 130 (and vice versa). Rod 140 is substantially similar to rods 30, 120, and/or 130 except that the distal end 142 of rod 140 is constructed of a soft material. Rod 140 is constructed of two different materials. A distal end 142 of rod 140 is constructed of a low durometer material, such as silicone, that is flexible. The remainder of rod 140 is constructed of a higher durometer material, e.g., a high durometer polymer or a metal, that is relatively stiff to permit tunneling through subcutaneous tissue or other structures of the body of patient 12. Toward the distal end 142 of rod 140, the higher durometer material includes a portion that has a smaller diameter than the proximal end of rod 140 and extends within the lower durometer material of distal end 142. A rod 140 with such a construction may be particularly useful when tunneling rod 140 underneath or below the sternum in the substernal, retrosternal, extravascular locations to avoid puncturing the pleura and/or pericardium or others structure in those locations.

In the example illustrated in FIG. 14, the distal end 142 of rod 140 is a solid piece of low durometer material. In some instances, one or more radiopaque markers may be added at one or more locations of the distal end 142 or a radiopaque additive maybe added to the polymer to allow visualization of the distal end 142. For example, fluoroscopy may be used to determine the shape and deflection of the distal end 142 of rod 140 during tunneling. This may be particularly useful when tunneling underneath or below the sternum in the substernal, retrosternal, or other extravascular locations.

Figure 15:
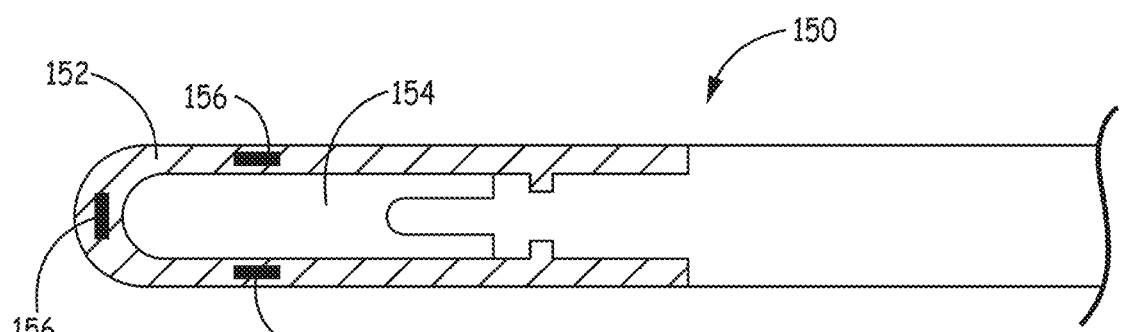
FIG. 15 illustrates a distal portion of another example rod.

FIG. 15 illustrates a distal portion of another alternative rod 150. Rod 150 can include one or more of the structure and/or functionality of rods 30, 120, 130 and/or 140 (and vice versa). The distal portion of rod 150 is substantially to the distal portion of rod 140 except that the distal end 152 of rod 150 is not constructed of a solid piece of material. Instead, distal end 152 forms an air cavity 154 within the soft, low durometer material of distal end 152. Distal end 152 of rod 150 is illustrated as including a plurality of radiopaque markers 156 within the low durometer material. Radiopaque markers 156 may be placed such that a user may visualize the location and/or deflection of the distal end 156, e.g., using fluoroscopy. This again may be particularly useful when tunneling underneath or below the sternum in the substernal, retrosternal, extravascular locations. In other instances, the material used to form distal end may include a low durometer material that has a radiopaque additive.

Various examples have been described. These and other examples are within the scope of the following claims.

The invention claimed is:

1. A system comprising:
   a medical lead, wherein the medical lead comprises:
      a lead body having a proximal end and a distal end, wherein the proximal end of the lead body is configured to connect to a medical device, and wherein the distal end of the lead body includes one or more electrodes; and
   an implant tool for implanting the medical lead, wherein the implant tool comprises:
      a rod that includes:
         a handle;
         a shaft having a proximal end adjacent to the handle and a distal end, wherein the shaft is formed with a groove that extends into the shaft to define an attachment feature toward the distal end of the shaft, the attachment feature configured to couple to the medical lead; and
      a sheath configured to be placed on the rod, wherein the sheath includes a body having proximal end and a distal end, and further wherein the sheath is configured to be placed in multiple positions along the rod including a first position in which the sheath does not interact with the attachment feature and second position in which the sheath does interact with the attachment feature.

2. The system of claim 1, wherein the attachment feature comprises a hook feature defined by the groove that extends into the shaft and is configured to receive an attachment feature of the medical lead, wherein in the first position the sheath does not cover the hook feature and in the second position the sheath does cover the hook feature.

3. The system of claim 2, wherein the shaft is formed with a groove that extends into the shaft at an angle to define the hook feature.

4. The system of claim 1, wherein the attachment feature defined by the groove comprises a recess that extends into the distal end of the shaft of the rod, the recess being configured to receive and couple to a portion of the medical lead, wherein in the first position the sheath does not extend beyond the distal end of the shaft of the rod and in the second position the sheath does extend beyond the distal end of the shaft of the rod.

5. The system of claim 4, wherein the recess is configured to receive and couple to a terminal pin of a connector on the proximal end of the medical lead.

6. The system of claim 5, wherein the shaft is formed with a groove that extends across a diameter of the distal end of the shaft and has a round recess that extends into a center of the distal end of the rod and is sized to be equal to or slightly smaller than a diameter of a terminal pin of a connector of the medical lead.

7. The system of claim 1, wherein the sheath includes a handle at the proximal end of the body, wherein the handle of the sheath is configured to lock the sheath in the multiple positions.

8. The of claim 7, wherein the handle of the sheath includes at least a first groove and a second groove spaced apart from one another by a distance, wherein the first and second grooves are shaped to receive a portion of the handle of the rod such that when the portion of the handle of the rod is placed within the first groove the sheath is locked in the first position and when the portion of the handle of the rod is placed within the second groove the sheath is locked in the second position.

9. The system of claim 1, wherein the multiple positions include a third position in which the sheath extends beyond the distal end of the shaft of the rod.

10. The system of claim 1, wherein the sheath includes an opening that extends along the body of the sheath from the proximal end to the distal end, wherein an inner channel of the sheath is accessible via the opening.

11. The system of claim 1, wherein the sheath comprises a splittable sheath having one or more score lines.

12. The system of claim 1, wherein the sheath comprises a slittable sheath.

13. The system of claim 1, wherein the shaft of the rod has a diameter that is greater than a diameter of the medical lead and the body of the sheath has an inner diameter that is less than or equal to the diameter of rod such that the sheath and shaft of the rod create an interference fit.

14. The system of claim 13, wherein the sheath is held in the multiple positions along the shaft of the rod via the interference fit.

15. The system of claim 1, wherein at least one of the shaft of the rod and the body of the sheath includes one or more markings that identify locations that coincide with locations of features of the medical lead when the medical lead is placed within the sheath such that a distal end of the medical lead is located at the distal end of the body of the sheath.

16. The system of claim 15, wherein the one or more markings identify locations that coincide with locations of one or more electrodes of the medical lead when the medical lead is placed within the sheath such that a distal end of the medical lead is located at the distal end of the body of the sheath.

17. The system of claim 16,
   wherein the one or more markings identify locations that coincide with locations of the one or more electrodes of the medical lead when the medical lead is placed within the sheath such that a distal end of the medical lead is located at the distal end of the body of the sheath.

18. The system of claim 1, wherein a first outer diameter of the shaft distal to the attachment feature is less than or approximately equal to a second outer diameter of the shaft proximal to the attachment feature.

19. The system of claim 1, wherein the distal end of the shaft of the rod is rounded.

20. A system comprising:
   a medical lead; and
   an implant tool for implanting the medical lead, the implant tool comprising:
      a rod that includes:
         a handle;
         a shaft having a proximal end adjacent to the handle and a distal end, wherein the shaft of the rod has a diameter that is greater than a diameter of the medical lead, and wherein the shaft is formed with a groove that extends into the shaft to define an attachment feature toward the distal end of the shaft, the attachment feature configured to couple to the medical lead; and a sheath configured to be placed on the rod, wherein the sheath includes a body having proximal end and a distal end, the body of the sheath having an inner diameter that is less than or equal to the diameter of the rod such that the sheath and shaft of the rod create an interference fit, and further wherein the sheath is configured to be placed in multiple positions along the rod including a first position in which the sheath does not interact with the attachment feature and second position in which the sheath does interact with the attachment feature.

21. The system of claim 20, wherein the sheath is held in the multiple positions along the shaft of the rod via the interference fit.

22. A system comprising:
a rod that includes:
a handle;
a shaft having a proximal end adjacent to the handle and a distal end, wherein the shaft is formed with a groove that extends into the shaft to define an attachment feature toward the distal end of the shaft, the attachment feature configured to couple to the medical lead;
a sheath configured to be placed on the rod, wherein the sheath includes a body having proximal end and a distal end, and further wherein the sheath is configured to be placed in multiple positions along the rod including a first position in which the sheath does not interact with the attachment feature and second position in which the sheath does interact with the attachment feature; and
an implantable medical lead that includes one or more electrodes along a distal portion of the medical lead, wherein at least one of the shaft of the rod and the body of the sheath includes one or more markings that identify locations that coincide with locations of the one or more electrodes of the medical lead when the medical lead is placed within the sheath such that a distal end of the medical lead is located at the distal end of the body of the sheath.

* * * * *